United States Patent [19]

Vierling, Jr.

[11] Patent Number: 5,840,558

[45] Date of Patent: Nov. 24, 1998

[54] SOYBEAN PEROXIDASE GENE FAMILY AND AN ASSAY FOR DETECTING SOYBEAN PEROXIDASE ACTIVITY

[75] Inventor: Richard A. Vierling, Jr., Lafayette, Ind.

[73] Assignee: Indiana Crop Improvement Association, Layfayette, Ind.

[21] Appl. No.: 671,320

[22] Filed: Oct. 27, 1995

[51] Int. Cl.$^6$ .............................. C12N 9/08; C12N 1/20; C12N 15/09; C07H 21/04

[52] U.S. Cl. ................. 435/192; 435/252.3; 435/320.1; 435/415; 536/23.2; 536/24.3

[58] Field of Search ................... 536/23.2, 24.3; 435/240.1, 320.1, 192, 252.3, 415

[56] References Cited

U.S. PATENT DOCUMENTS 5,112,752  5/1992  Johnson et al. .......................... 435/192

OTHER PUBLICATIONS

Scharff, M. et al.: *Hospital Practice*, Hybridomas As a Source of Antibodies, pp. 61–66 (Jan. 1981).

*Primary Examiner*—Robert A. Wax
*Assistant Examiner*—Elizabeth Slobodyansky
*Attorney, Agent, or Firm*—Rothwell, Figg, Ernst & Kurz, p.c.

[57] ABSTRACT

Four cDNA sequences representing a soybean peroxidase gene family are provided. An enzyme-capture assay for the nondestructive, sensitive and reliable quantitation of peroxidase activity is also provided. Cultivars having a high-peroxidase level can be efficiently selected, providing a large, renewable source of peroxidase for use in industry and in diagnostic chemistries.

10 Claims, 10 Drawing Sheets

```
                                          sEP a1  ATG GGA AGC
                                          sEP a2  ... ... ...
                                             p1    M   G   S
                                             p2    .   .   .
AAC TTG AGG TTT TTG AGT CTT TGC CTC TTG GCA TTG ATT GCA TCG ACT CAT GCT
... ..C ... ... ... ... ... ... ... ... ... ... ... ..A ..C ... ...      -1
 N   L   R   F   L   S   L   C   L   L   A   L   I   A   S   T   H   A
 .   F   .   .   .   .   .   .   .   .   .   .   .   .   .   .   .   .
CAA CTT CAG CTT GGT TTT TAT GCT AAC AGT TGC CCA AAA GCA GAG CAA ATT GTT
... ... ... ... ... ... ... ... ..C ..G ... ... ... ..C ..T ... ..C ...
 Q   L   Q   L   G   F   Y   A   N   S   C   P   K   A   E   Q   I   V   18
 .   .   .   .   .   .   .   .   K   .   .   N   .   .   .   .   .   .
TTG AAA TTT GTT CAT GAC CAT ATC CAC AAT GCT CCA TCA CTA GCA GCA GCA TTA
... ... ... ... ...-..C ... ... ... ... ... ... ... ... ... ... ... ..G
 L   K   F   V   H   D   H   I   H   N   A   P   S   L   A   A   A   L   36
 .   .   .   .   .   .   .   .   .   .   .   .   .   .   .   .   .   .
ATA AGA ATG CAC TTT CAT GAC TGT TTT GTA AGG GGA TGT GAT GCA TCA GTC CTT
... ... ... ... ... ..C ... ... ... ... ... ... ... ... ... ... ... ...
 I   R   M  |H   F   H   D   C   F   V| R   G   C   D   A   S   V   L   54
 .   .   .   .   .   .   .   .   .   .   .   .   .   .   .   .   .   .
CTG AAC TCA ACA ACC AAT CAG GCT GAG AAG AAT GCT CCT CCA AAT CTC ACA GTA
... ... ... ... ... ..A ... ..A ... ... ... ... ... ... ... ... ... ...
 L   N   S   T   T   N   Q   A   E   K   N   A   P   P   N   L   T   V   72
 .   .   .   .   .   .   .   .   .   .   .   .   .   .   .   .   .   .
AGA GGC TTT GAC TTC ATT GAC AGA ATA AAG AGC CTT GTT GAA GCT GAA TGC CCT
... ... ... ... ... ... ... ... ... ... ... ..G ...A ... ... ... ... ...
 R   G   F   D   F   I   D   R   I   K   S   L   V   E   A   E   C   P   90
 .   .   .   .   .   .   .   .   .   .   .   .   .   .   .   .   .   .
GGT GTG GTC TCT TGT GCT GAT ATC CTC ACT TTG GCT GCC AGA GAC ACT ATT GTA
... ... ... ... ... ... ... ... ... ... T.. ... ... ... ... ... ... ...
 G   V   V   S   C   A   D   I   L   T   L   A| A   R   D   T   I   V   108
 .   .   .   .   .   .   .   .   .   .   .   S  .   .   .   .   .   .
GCC ACA GGT GGA CCT TTT TGG AAA GTT CCA ACT GGT CGA AGG GAT GGG GTC GTC
... ... ... ..A ... ... ... ... ... ..A ... ... ..A ... ... ... ... A..
 A   T   G   G   P   F   W   K   V   P   T   G   R   R   D   G   V   V   126
 .   .   .   .   .   .   .   .   .   .   .   .   .   .   .   .   .   I
TCT AAC TTG ACG GAA GCC AGA AAT AAC ATT CCT GCT CCA TCT TCC AAC TTT ACC
... ... ... ... ... ... ...G... ... ... ... ... ... ... ..T ... ... ...
 S   N   L   T   E   A   R   N   N   I   P   A   P   S   S   N   F   T   144
 .   .   .   .   .   .   .   D   .   .   .   .   .   .   .   .   .   .
```

FIG. 5A

```
ACC CTA CAA ACA CTC TTT GCT AAC CAA GGA CTT GAT TTG AAG GAC TTG GTC CTG
... ... ... ... ... ... ..C ... ... ... ... ... ... ... ... ... ...
 T   L   Q   T   L   F   A   N   Q   G   L   D   L   K  |D   L   V   L| 162
 .   .   .   .   .   .   .   .   .   .   .   .   .   .   .   .   .   .
CTC TCT GGT GCT CAC ACA ATT GGT ATC GCT CAT TGC TCA TCA TTA TCA AAC CGG
... ... ... ... ... ... ... ... ... ... ... ... ..G ... ... ... ... ..C
|L   S   G   A   H   T   I|  G   I   A   H   C   S   S   L   S   N   R  180
 .   .   .   .   .   .   .   .   .   .   .   .   .   .   .   .   .   .
TTG TTC AAT TTC ACT GGC AAG GGT GAT CAA GAC CCG TCA CTA GAT AGT GAA TAT
... ... ... ... ... ... ... ... ... ... ... ... ..T ..C ... ... ... ...
 L   F   N   F   T   G   K   G   D   Q   D   P   S   L   D   S   E   Y  198
 .   .   .   .   .   .   .   .   .   .   .   .   .   .   .   .   .   .
GCT GCA AAT TTG AAA GCA TTC AAG TGC ACA GAC CTC AAC AAG TTG AAC ACC ACA
... ... ... ..C ... ... ..C ... ... ... ..G ... ... ..T ... ... ... ...
 A   A   N   L   K   A   F   K   C   T   D   L   N   K   L   N   T   T  216
 .   .   .   .   .   .   .   .   .   .   .   .   .   .   .   .   .   .
AAA ATT GAG ATG GAC CCT GGA AGT CGC AAG ACA TTT GAT CTT AGC TAC TAT AGT
... ... ... ... ... ... ... ... ... ... ... ... ... ... ... ... ... ...
 K   I   E   M   D   P   G   S   R   K   T   F   D   L   S   Y   Y   S  234
 .   .   .   .   .   .   .   .   .   .   .   .   .   .   .   .   .   .
CAC GTT ATT AAG AGA AGG GGT CTA TTT GAG TCA GAT GCT GCA TTA TTG ACT AAC
... ... ... ... ... ... ... ... ... ... ... ... ... ... ..G ... ..A ...
 H   V   I   K   R   R   G   L   F   E   S   D   A   A   L   L   T   N  252
 .   .   .   .   .   .   .   .   .   .   .   .   .   .   .   .   .   .
TCA GTT ACA AAG GCA CAA ATC ATC CAA TTG CTT GAA GGG TCA GTT GAA AAT TTC
... ... ... ... ..G ... ... ... ..T ..G ... ... ... ... ... ... ... ...
 S   V   T   K   A   Q   I   I   Q   L   L   E   G   S   V   E   N   F  270
 .   .   .   .   .   .   .   .   E   .   .   .   .   .   .   .   .   .
TTT GCT GAG TTT GCA ACC TCC ATC GAG AAA ATG GGA AGA ATT AAT GTG AAG ACA
... ... ... ... ... ... ... ..G ... ... ... ... ... ... ... ... ... ...
 F   A   E   F   A   T   S   I   E   K   M   G   R   I   N   V   K   T  288
 .   .   .   .   .   .   .   M   .   .   .   .   .   .   .   .   .   .
GGC ACA GAA GGA GAG ATC AGG AAG CAT TGT GCA TTT ATA AAT AGC TAA
..G ... ... ... ... ... ... ... ... ..C ... ... ... ... ... ...
 G   T   E   G   E   I   R   K   H   C   A   F   I   N   S   end
 .   .   .   .   .   .   .   .   .   .   .   .   L   .   .   end
```

FIG. 5B

```
                                          sEP b1  ATG GCT GTC ATG
                                          sEP b2  ... ... ... ...
                                             p3    M   A   V   M
                                             p4    .   .   .   .
GGT GCA TTC TTG AAT TTG ATC ATC *** TTT TCA GTA GTC TCT ACA ACA GGC AAG
... ... ... ... ... ... ... ... ATG ... ... ... ... ... *** ... ... ...
 V   A   F   L   N   L   I   I   *   F   S   V   V   S   T   T   G   K   -1
 .   .   .   .   .   .   .   .   M   .   .   .   .   .   *   .   .   .
TCA CTG AGC TTA AAC TAC TAT GCA AAA ACA TGC CCT AAT GTG GAG TTC ATT GTT
... ... ... ... ... ... T.. ... ... ... ... ... G.. ... ..A .G. ... ...
 S   L   S   L   N   Y   Y   A   K   T   C   P   N   V   E   F   I   V   18
 .   .   .   .   .   .   .   .   S   .   .   .   D   .   .   C   .   .
GCC AAC GCA GTA AAG GAT GCC ACT GCT AGG GAC AAA ACT GTT CCA GCA GCA ATT
... ... ..G ... ... ... ... ... ... ... ... ... ... ... ..T ... C.. ...
 A   K   A   V   K   D   A   T   A   R   D   K   T   V   P   A   A   I   36
 .   .   .   .   .   .   .   .   .   .   .   .   .   .   .   .   .   L
CTG CGA ATG CAC TTC CAT GAT TGT TTC GTT CGG GGG TGT GAT GCC TCT GTG CTG
... ... ... ... ... ... ..C ... ... ... ... ... ... .G. ... ... ... ...
 L   R   M  |H   F   H   D   C   F   V|  R   G   C   D   A   S   V   L   54
 .   .   .   .   .   .   .   .   .   .   .   G   .   .   .   .   .   .
CTA AAT TCA AAA GGA AAC AAC AAA GCA GAA AAA GAC GGG CCA CCA AAT GTT TCT
... ... ... ... ... ..G ... ... ... ... ... ..T ... ... ... ... ... ...
 L   N   S   K   G   N   N   K   A   E   K   D   G   P   P   N   V   S   72
 .   .   .   .   .   S   .   .   .   .   .   .   .   .   .   .   .   .
TTG CAT GCA TTC TAT GTC ATT GTA GCA GCA AAG AAA GCA CTA GAA GCT TCA TGC
... ... ... ... ... ... .AT ... ..G ... ... ... ... ... ... ... ... ...
 L   H   A   F   Y   V   I   V   A   A   K   K   A   L   E   A   S  |C|  90
 .   .   .   .   .   .   .   D   .   .   .   .   .   .   .   .   .   .
CCT GGT GTG GTC TCT TGT GCT GAC ATC CTT GCT CTG GCA GCA AGG GTC GCA GTT
..A ... ... ... ... ... ... ... ... ... ... ..A ... ... ... .AT ... ...
|P   G   V   V   S   C   A   D   I   L   A   L   A|  R   V   A   V   ##
 .   .   .   .   .   .   .   .   .   .   .   .   .   .   D   .   .
TTT CTG TCA GGA GGA CCT ACA TGG GAT GTT CCT AAA GGA AGA AAG GAT GGT AGA
... ... ... ... ... ... ... ... .AA ... ... ... ... ... ... ..C ... ...
 F   L   S   G   G   P   T   W   D   V   P   K   G   R   K   D   G   R   ##
 .   .   .   .   .   .   .   .   E   .   .   .   .   .   .   .   .   .
ACA TCT AAA GCC AGT GAA ACC AGA CAA TTG CCA GCA CCA ACC TTC AAC TTA TCA
... ... ... ..C ... ... ... ..A ... ... ... ... ... ... ... ... ... ...
 T   S   K   A   S   E   T   R   Q   L   P   A   P   T   F   N   L   S   ##
 .   .   .   .   .   .   .   .   .   .   .   .   .   .   .   .   .   .
```

FIG. 6A

```
CAA CTG CGG CAA AGT TTC TCT CAA AGA GGA CTG TCA GGG GAA GAC CTG GTA GCT
... ... ... ... ...C ... ... ... ... ... ... ... ... ... ... ... ...
 Q   L   R   Q   S   F   S   Q   R   G   L   S   G   E  |D   L   V   A  ##
 .   .   .   .   .   .   .   .   .   .   .   .   .   .  |.   .   .   .
CTG TCA GGG GGG CAC ACT TTG GGT TTC TCT CAC TGC TCA TCT TTC AAG AAC AGA
... ... ... ... ... ... ... ... ... ... ... ... ... ... ... ... ... ...
 L   S   G   G   H   T |L   G   F   S   H   C   S   S   F   K   N   R  ##
 .   .   .   .   .   . |.   .   .   .   .   .   .   .   .   .   .   .
ATC CAC AAC TTC AAT GCA ACA CAT GAT GTT GAC CCT TCA TTA AAT CCA TCA TTT
... ... ... ... ... ...T ... ... ... ... .AA ... ... ... ... ... ... ...
 I  -H   N   F   N   A   T   H   D   V   D   P   S   L   N   P   S   F  ##
 .   .   .   .   .   .   .   .   E   .   .   .   .   .   .   .   .   .
GCA GCA AAA CTG ATC TCA ATT TGT CCA CTA AAA AAT CAG GCA AAA AAT GCA GGC
...A... ... ... ...A... ... ... ... ... ... ... ... ... ... ... ... ...
 A   A   K   L   I   S   I   C   P   L   K   N   Q   A   K   N   A   G  ##
 .   T   .   .   .   .   .   .   .   .   .   .   .   .   .   .   .   .
ACC TCT ATG GAC CCT TCA ACA ACA ACT TTT GAT AAT ACA TAT TAC AGG TTG ATC
... ... ... ... ... ... ... ... ... ... ... ... ... ... ... ... ... ...
 T   S   M   D   P   S   T   T   T   F   D   N   T   Y   Y   R   L   I  ##
 .   .   .   .   .   .   .   .   .   .   .   .   .   .   .   .   .   .
CTC CAA CAG AAA GGC TTG TTT TCT TCT GAT CAA GTT TTG CTT GAC AAC CCA GAC
... ... ... ... ... ... ... ... ... ... ... ... ... ... ... ... ... ...
 L   Q   Q   K   G   L   F   S   S   D   Q   V   L   L   D   N   P   D  ##
 .   .   .   .   .   .   .   .   .   .   .   .   .   .   .   .   .   .
ACT AAA AAT CTG GTT ACA AAG TTT GCC ACC TCA AAA AAG GCT TTT TAT GAG GCT
... ... ... ... ...G.G... ... ... ... ... ... ... ... ... ... ...C ...
 T   K   N   L   V   T   K   F   A   T   S   K   K   A   F   Y   E   A  ##
 .   .   .   .   .   A   .   .   .   .   .   .   .   .   .   .   D   .
TTT GCG AAG TCC ATG ATC AGA ATG AGT AGC TAC AAT GGT GGA CAG GAG GTT AGA
... ... ... ... ... ... ...A... ... ... ...AT ... ... ... ... ... ...
 F   A   K   S   M   I   R   M   S   S   Y   N   G   G   Q   E   V   R  ##
 .   .   .   .   .   .   .   K   .   .   I   .   .   .   .   .   .   .
AGG ACT GCA GAA TGA
... ... ... ...G ...
 R   T   A   E  end
 .   .   .   .  end
```

FIG. 6B

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

His  Phe  His  Asp  Cys  Phe  Val
    1                       5

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 3

(D) OTHER INFORMATION: /note= "Location 3 can be either C or T"

(ix) FEATURE:
 (A) NAME/KEY: misc_feature
 (B) LOCATION: 6
 (D) OTHER INFORMATION: /note= "Location 6 can be either T or C"

(ix) FEATURE:
 (A) NAME/KEY: misc_feature
 (B) LOCATION: 9
 (D) OTHER INFORMATION: /note= "Location 9 can be either C or T"

(ix) FEATURE:
 (A) NAME/KEY: misc_feature
 (B) LOCATION: 12
 (D) OTHER INFORMATION: /note= "Location 12 can be either C or T"

(ix) FEATURE:
 (A) NAME/KEY: misc_feature
 (B) LOCATION: 15
 (D) OTHER INFORMATION: /note= "Location 15 can be either C or T"

(ix) FEATURE:
 (A) NAME/KEY: misc_feature
 (B) LOCATION: 18
 (D) OTHER INFORMATION: /note= "Location 18 can be either C or T"

(xi) SEQUENCE DESCRIPTION: SEQ ID NO:2:

CACTTTCACG ACTGCTTCGT   20

(2) INFORMATION FOR SEQ ID NO:3:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:3:

AAATTAACTC AGCTGTGGG   19

(2) INFORMATION FOR SEQ ID NO:4:

(i) SEQUENCE CHARACTERISTICS:
  (A) LENGTH: 20 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:4:

GGAACCCACT TATTCCATCG   20

(2) INFORMATION FOR SEQ ID NO:5:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: cDNA (xi) SEQUENCE DESCRIPTION: SEQ ID NO:5:

CCCAAGACAT GCTTGAGAT 19

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

AAGTTCATAC TTCTAAC 17

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Gln Leu Xaa Xaa Xaa Phe Tyr
1                    5

(2) INFORMATION FOR SEQ ID NO:8:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Ala Ala Thr Ala Ala Ala
1              5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

His Phe His Asp Cys Phe Val
1                  5

(2) INFORMATION FOR SEQ ID NO:10:

(i) SEQUENCE CHARACTERISTICS:
        (A) LENGTH: 1315 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..82

( i x ) FEATURE:
    ( A ) NAME/KEY: CDS
    ( B ) LOCATION: 83..1054

( i x ) FEATURE:
    ( A ) NAME/KEY: 3'UTR
    ( B ) LOCATION: 1055..1315

( i x ) FEATURE:
    ( A ) NAME/KEY: sig_peptide
    ( B ) LOCATION: 83..145

( i x ) FEATURE:
    ( A ) NAME/KEY: mat_peptide
    ( B ) LOCATION: 146..1054

( x i ) SEQUENCE DESCRIPTION: SEQ ID NO:10:

```
GAAGCATCTG  AGTGTTTACT  ATTTTGTACT  ATATTTATAT  ATAGTCACTC  AAGCTTCTAG                  60

GATTTCTGCC  TGCTGCATCA  AA ATG GGA AGC AAC TTG AGG TTT TTG AGT CTT                     112
                          Met Gly Ser Asn Leu Arg Phe Leu Ser Leu
                          -21 -20                          -15

TGC CTC TTG GCA TTG ATT GCA TCG ACT CAT GCT CAA CTT CAG CTT GGT                         160
Cys Leu Leu Ala Leu Ile Ala Ser Thr His Ala Gln Leu Gln Leu Gly
    -10              -5                   1                    5

TTT TAT GCT AAC AGT TGC CCA AAA GCA GAG CAA ATT GTT TTG AAA TTT                         208
Phe Tyr Ala Asn Ser Cys Pro Lys Ala Glu Gln Ile Val Leu Lys Phe
                10                  15                      20

GTT CAT GAC CAT ATC CAC AAT GCT CCA TCA CTA GCA GCT GCA TTA ATA                         256
Val His Asp His Ile His Asn Ala Pro Ser Leu Ala Ala Ala Leu Ile
            25                  30                      35

AGA ATG CAC TTT CAT GAC TGT TTT GTA AGG GGA TGT GAT GCA TCA GTC                         304
Arg Met His Phe His Asp Cys Phe Val Arg Gly Cys Asp Ala Ser Val
        40                  45                  50

CTT CTG AAC TCA ACA ACC AAT CAG GCT GAG AAG AAT GCT CCT CCA AAT                         352
Leu Leu Asn Ser Thr Thr Asn Gln Ala Glu Lys Asn Ala Pro Pro Asn
    55                  60                  65

CTC ACA GTA AGA GGC TTT GAC TTC ATT GAC AGA ATA AAG AGC CTT GTT                         400
Leu Thr Val Arg Gly Phe Asp Phe Ile Asp Arg Ile Lys Ser Leu Val
70                  75                  80                  85

GAA GCT GAA TGC CCT GGT GTG GTC TCT TGT GCT GAT ATC CTC ACT TTG                         448
Glu Ala Glu Cys Pro Gly Val Val Ser Cys Ala Asp Ile Leu Thr Leu
                90                  95                  100

GCT GCC AGA GAC ACT ATT GTA GCC ACA GGT GGA CCT TTT TGG AAA GTT                         496
Ala Ala Arg Asp Thr Ile Val Ala Thr Gly Gly Pro Phe Trp Lys Val
            105                 110                 115

CCA ACT GGT CGA AGG GAT GGG GTC GTC TCT AAC TTG ACG GAA GCC AGA                         544
Pro Thr Gly Arg Arg Asp Gly Val Val Ser Asn Leu Thr Glu Ala Arg
        120                 125                 130

AAT AAC ATT CCT GCT CCA TCT TCC AAC TTT ACC ACC CTA CAA ACA CTC                         592
Asn Asn Ile Pro Ala Pro Ser Ser Asn Phe Thr Thr Leu Gln Thr Leu
    135                 140                 145

TTT GCT AAC CAA GGA CTT GAT TTG AAG GAC TTG GTC CTG CTC TCT GGT                         640
Phe Ala Asn Gln Gly Leu Asp Leu Lys Asp Leu Val Leu Leu Ser Gly
150                 155                 160                 165

GCT CAC ACA ATT GGT ATC GCT CAT TGC TCA TCA TTA TCA AAC CGG TTG                         688
Ala His Thr Ile Gly Ile Ala His Cys Ser Ser Leu Ser Asn Arg Leu
                170                 175                 180

TTC AAT TTC ACT GGC AAG GGT GAT CAA GAC CCG TCA CTA GAT AGT GAA                         736
Phe Asn Phe Thr Gly Lys Gly Asp Gln Asp Pro Ser Leu Asp Ser Glu
            185                 190                 195

TAT GCT GCA AAT TTG AAA GCA TTC AAG TGC ACA GAC CTC AAC AAG TTG                         784
Tyr Ala Ala Asn Leu Lys Ala Phe Lys Cys Thr Asp Leu Asn Lys Leu
        200                 205                 210
```

-continued

| | | | | | | | | | | | | | | | |
|---|---|---|---|---|---|---|---|---|---|---|---|---|---|---|---|
| AAC | ACC | ACA | AAA | ATT | GAG | ATG | GAC | CCT | GGA | AGT | CGC | AAG | ACA | TTT | GAT | 832
| Asn | Thr | Thr | Lys | Ile | Glu | Met | Asp | Pro | Gly | Ser | Arg | Lys | Thr | Phe | Asp |
| 215 | | | | | 220 | | | | | | 225 | | | | |
| CTT | AGC | TAC | TAT | AGT | CAC | GTT | ATT | AAG | AGA | AGG | GGT | CTA | TTT | GAG | TCA | 880
| Leu | Ser | Tyr | Tyr | Ser | His | Val | Ile | Lys | Arg | Arg | Gly | Leu | Phe | Glu | Ser |
| 230 | | | | | 235 | | | | | 240 | | | | | 245 |
| GAT | GCT | GCA | TTA | TTG | ACT | AAC | TCA | GTT | ACA | AAG | GCA | CAA | ATC | ATC | CAA | 928
| Asp | Ala | Ala | Leu | Leu | Thr | Asn | Ser | Val | Thr | Lys | Ala | Gln | Ile | Ile | Gln |
| | | | | 250 | | | | | 255 | | | | | 260 | |
| TTG | CTT | GAA | GGG | TCA | GTT | GAA | AAT | TTC | TTT | GCT | GAG | TTT | GCA | ACC | TCC | 976
| Leu | Leu | Glu | Gly | Ser | Val | Glu | Asn | Phe | Phe | Ala | Glu | Phe | Ala | Thr | Ser |
| | | | 265 | | | | | 270 | | | | | 275 | | |
| ATC | GAG | AAA | ATG | GGA | AGA | ATT | AAT | GTG | AAG | ACA | GGC | ACA | GAA | GGA | GAG | 1024
| Ile | Glu | Lys | Met | Gly | Arg | Ile | Asn | Val | Lys | Thr | Gly | Thr | Glu | Gly | Glu |
| | | 280 | | | | | 285 | | | | | 290 | | | |
| ATC | AGG | AAG | CAT | TGT | GCA | TTT | ATA | AAT | AGC | TAAGAATCTT | | GTCTTGGGGT | | | | 1074
| Ile | Arg | Lys | His | Cys | Ala | Phe | Ile | Asn | Ser | | | | | | |
| | 295 | | | | | 300 | | | | | | | | | |

TTGATTATTT ATGCTATGCC ATGTTTTTG ATTAGTTATG CTATGCCATG TGGTCTCTGT  1134
CTACATACGT GTGATCCTTT ATGGTATGGT TGTTGTATGT GTGTTGGAAT AAGTGGGCTC  1194
TTAAGTTATT CATATTTCCA ACTTTCCAAC TTTGCTGGTA GATCATGCTC TTGTAATAAG  1254
AACCAGAATT TTTTGTGCTA CCCACAGCTG AGTTAATTTA AAAAAAAAAA AAAAAAAAA  1314
A                                                                 1315

( 2 ) INFORMATION FOR SEQ ID NO:11:

( i ) SEQUENCE CHARACTERISTICS:
        ( A ) LENGTH: 324 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| | | | | | | | | | | | | | |
|---|---|---|---|---|---|---|---|---|---|---|---|---|---|
| Met | Gly | Ser | Asn | Leu | Arg | Phe | Leu | Ser | Leu | Cys | Leu | Leu | Ala | Leu | Ile |
| -21 | -20 | | | | | -15 | | | | -10 | | | | |
| Ala | Ser | Thr | His | Ala | Gln | Leu | Gln | Leu | Gly | Phe | Tyr | Ala | Asn | Ser | Cys |
| -5 | | | | | 1 | | | | 5 | | | | | 10 | |
| Pro | Lys | Ala | Glu | Gln | Ile | Val | Leu | Lys | Phe | Val | His | Asp | His | Ile | His |
| | | | 15 | | | | | 20 | | | | | 25 | | |
| Asn | Ala | Pro | Ser | Leu | Ala | Ala | Ala | Leu | Ile | Arg | Met | His | Phe | His | Asp |
| | | 30 | | | | | 35 | | | | | 40 | | | |
| Cys | Phe | Val | Arg | Gly | Cys | Asp | Ala | Ser | Val | Leu | Leu | Asn | Ser | Thr | Thr |
| | 45 | | | | | 50 | | | | | 55 | | | | |
| Asn | Gln | Ala | Glu | Lys | Asn | Ala | Pro | Pro | Asn | Leu | Thr | Val | Arg | Gly | Phe |
| 60 | | | | | 65 | | | | | 70 | | | | | 75 |
| Asp | Phe | Ile | Asp | Arg | Ile | Lys | Ser | Leu | Val | Glu | Ala | Glu | Cys | Pro | Gly |
| | | | | 80 | | | | | 85 | | | | | 90 | |
| Val | Val | Ser | Cys | Ala | Asp | Ile | Leu | Thr | Leu | Ala | Ala | Arg | Asp | Thr | Ile |
| | | | 95 | | | | | 100 | | | | | 105 | | |
| Val | Ala | Thr | Gly | Gly | Pro | Phe | Trp | Lys | Val | Pro | Thr | Gly | Arg | Arg | Asp |
| | | | 110 | | | | | 115 | | | | | 120 | | |
| Gly | Val | Val | Ser | Asn | Leu | Thr | Glu | Ala | Arg | Asn | Asn | Ile | Pro | Ala | Pro |
| | | 125 | | | | | 130 | | | | | 135 | | | |
| Ser | Ser | Asn | Phe | Thr | Thr | Leu | Gln | Thr | Leu | Phe | Ala | Asn | Gln | Gly | Leu |
| 140 | | | | | 145 | | | | | 150 | | | | | 155 |
| Asp | Leu | Lys | Asp | Leu | Val | Leu | Leu | Ser | Gly | Ala | His | Thr | Ile | Gly | Ile |

|     |     |     |     |     | 160 |     |     |     | 165 |     |     |     |     | 170 |
| --- | --- | --- | --- | --- | --- | --- | --- | --- | --- | --- | --- | --- | --- | --- |
| Ala | His | Cys | Ser | Ser | Leu | Ser | Asn | Arg | Leu | Phe | Asn | Phe | Thr | Gly | Lys |
|     |     |     | 175 |     |     |     |     | 180 |     |     |     | 185 |     |     |
| Gly | Asp | Gln | Asp | Pro | Ser | Leu | Asp | Ser | Glu | Tyr | Ala | Ala | Asn | Leu | Lys |
|     |     | 190 |     |     |     | 195 |     |     |     |     | 200 |     |     |     |
| Ala | Phe | Lys | Cys | Thr | Asp | Leu | Asn | Lys | Leu | Asn | Thr | Thr | Lys | Ile | Glu |
|     | 205 |     |     |     |     | 210 |     |     |     |     | 215 |     |     |     |
| Met | Asp | Pro | Gly | Ser | Arg | Lys | Thr | Phe | Asp | Leu | Ser | Tyr | Tyr | Ser | His |
| 220 |     |     |     |     | 225 |     |     |     |     | 230 |     |     |     |     | 235 |
| Val | Ile | Lys | Arg | Arg | Gly | Leu | Phe | Glu | Ser | Asp | Ala | Ala | Leu | Leu | Thr |
|     |     |     |     | 240 |     |     |     |     | 245 |     |     |     |     | 250 |
| Asn | Ser | Val | Thr | Lys | Ala | Gln | Ile | Ile | Gln | Leu | Leu | Glu | Gly | Ser | Val |
|     |     |     | 255 |     |     |     |     | 260 |     |     |     |     | 265 |     |
| Glu | Asn | Phe | Phe | Ala | Glu | Phe | Ala | Thr | Ser | Ile | Glu | Lys | Met | Gly | Arg |
|     |     | 270 |     |     |     |     | 275 |     |     |     |     | 280 |     |     |
| Ile | Asn | Val | Lys | Thr | Gly | Thr | Glu | Gly | Glu | Ile | Arg | Lys | His | Cys | Ala |
|     | 285 |     |     |     |     | 290 |     |     |     |     | 295 |     |     |     |
| Phe | Ile | Asn | Ser |
| 300 |     |     |     |

( 2 ) INFORMATION FOR SEQ ID NO:12:

( i ) SEQUENCE CHARACTERISTICS:
        ( A ) LENGTH: 1326 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..86

( i x ) FEATURE:
        ( A ) NAME/KEY: CDS
        ( B ) LOCATION: 87..1058

( i x ) FEATURE:
        ( A ) NAME/KEY: 3'UTR
        ( B ) LOCATION: 1059..1326

( i x ) FEATURE:
        ( A ) NAME/KEY: sig_peptide
        ( B ) LOCATION: 87..149

( i x ) FEATURE:
        ( A ) NAME/KEY: mat_peptide
        ( B ) LOCATION: 150..1058

( x i ) SEQUENCE DESCRIPTION: SEQ ID NO:12:

```
GCCTCTTTCA AGAAGCATCT GAGTGCTTAT TATTTGTAAT ATATATAGTC ACTCAAGCTT                60

CTAGGATTTG TGCCAGCTAC ATGAAA ATG GGA AGC AAC TTC AGG TTT TTG AGT               113
                             Met Gly Ser Asn Phe Arg Phe Leu Ser
                             -21 -20                         -15

CTT TGC CTC TTG GCA TTG ATT GCA TCA ACC CAT GCT CAA CTT CAG CTT               161
Leu Cys Leu Leu Ala Leu Ile Ala Ser Thr His Ala Gln Leu Gln Leu
        -10                 -5                   1

GGT TTT TAT GCC AAG AGT TGC CCA AAC GCT GAG CAA ATC GTT TTG AAA               209
Gly Phe Tyr Ala Lys Ser Cys Pro Asn Ala Glu Gln Ile Val Leu Lys
  5               10                  15                      20

TTT GTC CAT GAC CAT ATC CAC AAT GCT CCA TCA CTA GCA GCT GCA TTG               257
Phe Val His Asp His Ile His Asn Ala Pro Ser Leu Ala Ala Ala Leu
              25                  30                  35
```

| | | | | | | | | | | | | | | | | |
|---|---|---|---|---|---|---|---|---|---|---|---|---|---|---|---|---|
| ATA | AGA | ATG | CAC | TTC | CAT | GAC | TGT | TTT | GTA | AGG | GGA | TGT | GAT | GCA | TCA | 305 |
| Ile | Arg | Met | His | Phe | His | Asp | Cys | Phe | Val | Arg | Gly | Cys | Asp | Ala | Ser | |
| | | | 40 | | | | 45 | | | | | 50 | | | | |
| GTC | CTT | CTG | AAC | TCA | ACA | ACC | AAT | CAA | GCT | GAA | AAG | AAT | GCT | CCT | CCA | 353 |
| Val | Leu | Leu | Asn | Ser | Thr | Thr | Asn | Gln | Ala | Glu | Lys | Asn | Ala | Pro | Pro | |
| | | 55 | | | | | 60 | | | | | 65 | | | | |
| AAT | CTC | ACA | GTA | AGA | GGC | TTT | GAC | TTC | ATT | GAC | AGA | ATA | AAG | AGC | CTT | 401 |
| Asn | Leu | Thr | Val | Arg | Gly | Phe | Asp | Phe | Ile | Asp | Arg | Ile | Lys | Ser | Leu | |
| | | 70 | | | | 75 | | | | | 80 | | | | | |
| GTT | GAG | GCA | GAA | TGC | CCT | GGT | GTG | GTC | TCT | TGT | GCT | GAT | ATC | CTC | ACT | 449 |
| Val | Glu | Ala | Glu | Cys | Pro | Gly | Val | Val | Ser | Cys | Ala | Asp | Ile | Leu | Thr | |
| 85 | | | | | 90 | | | | | 95 | | | | | 100 | |
| TTG | TCT | GCC | AGA | GAC | ACT | ATT | GTA | GCC | ACA | GGT | GGA | CCA | TTT | TGG | AAA | 497 |
| Leu | Ser | Ala | Arg | Asp | Thr | Ile | Val | Ala | Thr | Gly | Gly | Pro | Phe | Trp | Lys | |
| | | | | 105 | | | | | 110 | | | | | 115 | | |
| GTT | CCA | ACA | GGT | CGA | AGA | GAT | GGG | GTC | ATC | TCT | AAC | TTG | ACG | GAA | GCC | 545 |
| Val | Pro | Thr | Gly | Arg | Arg | Asp | Gly | Val | Ile | Ser | Asn | Leu | Thr | Glu | Ala | |
| | | | 120 | | | | | 125 | | | | | 130 | | | |
| AGA | GAT | AAC | ATT | CCT | GCT | CCA | TCT | TCT | AAC | TTT | ACC | ACC | CTA | CAA | ACA | 593 |
| Arg | Asp | Asn | Ile | Pro | Ala | Pro | Ser | Ser | Asn | Phe | Thr | Thr | Leu | Gln | Thr | |
| | | 135 | | | | | 140 | | | | | 145 | | | | |
| CTC | TTT | GCC | AAC | CAA | GGA | CTT | GAT | TTG | AAG | GAC | TTG | GTC | CTG | CTC | TCT | 641 |
| Leu | Phe | Ala | Asn | Gln | Gly | Leu | Asp | Leu | Lys | Asp | Leu | Val | Leu | Leu | Ser | |
| | | 150 | | | | | 155 | | | | | 160 | | | | |
| GGT | GCT | CAC | ACA | ATT | GGT | ATC | GCT | CAT | TGC | TCA | TCA | TTG | TCA | AAC | CGC | 689 |
| Gly | Ala | His | Thr | Ile | Gly | Ile | Ala | His | Cys | Ser | Ser | Leu | Ser | Asn | Arg | |
| 165 | | | | | 170 | | | | | 175 | | | | | 180 | |
| TTG | TTC | AAT | TTC | ACT | GGC | AAG | GGT | GAT | CAA | GAC | CCG | TCA | TTA | GAC | AGT | 737 |
| Leu | Phe | Asn | Phe | Thr | Gly | Lys | Gly | Asp | Gln | Asp | Pro | Ser | Leu | Asp | Ser | |
| | | | | 185 | | | | | 190 | | | | | 195 | | |
| GAA | TAT | GCT | GCA | AAT | CTG | AAA | GCC | TTC | AAG | TGC | ACG | GAC | CTC | AAT | AAG | 785 |
| Glu | Tyr | Ala | Ala | Asn | Leu | Lys | Ala | Phe | Lys | Cys | Thr | Asp | Leu | Asn | Lys | |
| | | | 200 | | | | | 205 | | | | | 210 | | | |
| TTG | AAC | ACC | ACA | AAA | ATT | GAG | ATG | GAC | CCT | GGA | AGT | CGC | AAG | ACA | TTT | 833 |
| Leu | Asn | Thr | Thr | Lys | Ile | Glu | Met | Asp | Pro | Gly | Ser | Arg | Lys | Thr | Phe | |
| | | 215 | | | | | 220 | | | | | 225 | | | | |
| GAT | CTT | AGC | TAC | TAT | AGT | CAT | GTG | ATT | AAG | AGA | AGG | GGT | CTA | TTT | GAG | 881 |
| Asp | Leu | Ser | Tyr | Tyr | Ser | His | Val | Ile | Lys | Arg | Arg | Gly | Leu | Phe | Glu | |
| | | 230 | | | | | 235 | | | | | 240 | | | | |
| TCA | GAT | GCT | GCA | TTG | TTG | ACA | AAC | TCA | GTT | ACA | AAG | GCT | CAA | ATC | ATT | 929 |
| Ser | Asp | Ala | Ala | Leu | Leu | Thr | Asn | Ser | Val | Thr | Lys | Ala | Gln | Ile | Ile | |
| 245 | | | | | 250 | | | | | 255 | | | | | 260 | |
| GAA | TTG | CTT | GAA | GGG | TCA | GTT | GAA | AAT | TTC | TTT | GCT | GAG | TTT | GCA | ACC | 977 |
| Glu | Leu | Leu | Glu | Gly | Ser | Val | Glu | Asn | Phe | Phe | Ala | Glu | Phe | Ala | Thr | |
| | | | | 265 | | | | | 270 | | | | | 275 | | |
| TCC | ATG | GAG | AAA | ATG | GGA | AGA | ATT | AAT | GTA | AAG | ACA | GGG | ACA | GAA | GGA | 1025 |
| Ser | Met | Glu | Lys | Met | Gly | Arg | Ile | Asn | Val | Lys | Thr | Gly | Thr | Glu | Gly | |
| | | | 280 | | | | | 285 | | | | | 290 | | | |
| GAG | ATC | AGG | AAG | CAT | TGT | GCA | TTT | CTA | AAT | AGC | TAAGAATCTT | | GTCTTGTTCA | | | 1078 |
| Glu | Ile | Arg | Lys | His | Cys | Ala | Phe | Leu | Asn | Ser | | | | | | |
| | | 295 | | | | | 300 | | | | | | | | | |

TGGATGAATC TTGTATCATT TATTTTTGG GTTTGGTTAT TTATGCTATG CCATGTTTTT 1138

TTATTAGTTA TGCTATGCCA TGTGGTGTCT GTCTACATAT GAGTGATCCC GTATGGTATG 1198

GTTGTTGTAT GTGCGATGGA ATAAGTGGGT TCCATTGTTA TTCTTATAAT TTCCAACTTT 1258

GCTGGTAGAT CTTGTAATAA GAAGCAGAAT TTCTTGTGCT AAAAAAAAAA AAAAAAAAA 1318

AAAAAAAA 1326

( 2 ) INFORMATION FOR SEQ ID NO:13:

(i) SEQUENCE CHARACTERISTICS:
    (A) LENGTH: 324 amino acids
    (B) TYPE: amino acid
    (D) TOPOLOGY: linear (ii) MOLECULE TYPE: protein (xi) SEQUENCE DESCRIPTION: SEQ ID NO:13:

| Met -21 | Gly -20 | Ser | Asn | Phe | Arg | Phe -15 | Leu | Ser | Leu | Cys | Leu -10 | Leu | Ala | Leu | Ile |
|---|---|---|---|---|---|---|---|---|---|---|---|---|---|---|---|
| Ala -5 | Ser | Thr | His | Ala | Gln 1 | Leu | Gln | Leu | Gly 5 | Phe | Tyr | Ala | Lys | Ser 10 | Cys |
| Pro | Asn | Ala | Glu 15 | Gln | Ile | Val | Leu | Lys 20 | Phe | Val | His | Asp | His 25 | Ile | His |
| Asn | Ala | Pro 30 | Ser | Leu | Ala | Ala | Ala 35 | Leu | Ile | Arg | Met | His 40 | Phe | His | Asp |
| Cys | Phe 45 | Val | Arg | Gly | Cys | Asp 50 | Ala | Ser | Val | Leu | Leu 55 | Asn | Ser | Thr | Thr |
| Asn 60 | Gln | Ala | Glu | Lys | Asn 65 | Ala | Pro | Pro | Asn | Leu 70 | Thr | Val | Arg | Gly | Phe 75 |
| Asp | Phe | Ile | Asp | Arg 80 | Ile | Lys | Ser | Leu | Val 85 | Glu | Ala | Glu | Cys | Pro 90 | Gly |
| Val | Val | Ser | Cys 95 | Ala | Asp | Ile | Leu | Thr 100 | Leu | Ser | Ala | Arg | Asp 105 | Thr | Ile |
| Val | Ala | Thr 110 | Gly | Gly | Pro | Phe | Trp 115 | Lys | Val | Pro | Thr | Gly 120 | Arg | Arg | Asp |
| Gly | Val 125 | Ile | Ser | Asn | Leu | Thr 130 | Glu | Ala | Arg | Asp | Asn 135 | Ile | Pro | Ala | Pro |
| Ser 140 | Ser | Asn | Phe | Thr | Thr 145 | Leu | Gln | Thr | Leu | Phe 150 | Ala | Asn | Gln | Gly | Leu 155 |
| Asp | Leu | Lys | Asp | Leu 160 | Val | Leu | Leu | Ser | Gly 165 | Ala | His | Thr | Ile | Gly 170 | Ile |
| Ala | His | Cys | Ser 175 | Ser | Leu | Ser | Asn | Arg 180 | Leu | Phe | Asn | Phe | Thr 185 | Gly | Lys |
| Gly | Asp | Gln 190 | Asp | Pro | Ser | Leu | Asp 195 | Ser | Glu | Tyr | Ala | Ala 200 | Asn | Leu | Lys |
| Ala | Phe 205 | Lys | Cys | Thr | Asp | Leu 210 | Asn | Lys | Leu | Asn | Thr 215 | Thr | Lys | Ile | Glu |
| Met 220 | Asp | Pro | Gly | Ser | Arg 225 | Lys | Thr | Phe | Asp | Leu 230 | Ser | Tyr | Tyr | Ser | His 235 |
| Val | Ile | Lys | Arg | Arg 240 | Gly | Leu | Phe | Glu | Ser 245 | Asp | Ala | Ala | Leu | Leu 250 | Thr |
| Asn | Ser | Val | Thr 255 | Lys | Ala | Gln | Ile | Ile 260 | Glu | Leu | Leu | Glu | Gly 265 | Ser | Val |
| Glu | Asn | Phe 270 | Phe | Ala | Glu | Phe | Ala 275 | Thr | Ser | Met | Glu | Lys 280 | Met | Gly | Arg |
| Ile | Asn 285 | Val | Lys | Thr | Gly | Thr 290 | Glu | Gly | Glu | Ile | Arg 295 | Lys | His | Cys | Ala |
| Phe 300 | Leu | Asn | Ser | | | | | | | | | | | | |

(2) INFORMATION FOR SEQ ID NO:14:

(i) SEQUENCE CHARACTERISTICS:
    (A) LENGTH: 1191 base pairs
    (B) TYPE: nucleic acid
    (C) STRANDEDNESS: single (D) TOPOLOGY: linear (ii) MOLECULE TYPE: cDNA (ix) FEATURE:
    (A) NAME/KEY: 5'UTR
    (B) LOCATION: 1..59

(ix) FEATURE:
    (A) NAME/KEY: CDS
    (B) LOCATION: 60..998

(ix) FEATURE:
    (A) NAME/KEY: 3'UTR
    (B) LOCATION: 999..1191

(ix) FEATURE:
    (A) NAME/KEY: sig_peptide
    (B) LOCATION: 60..122

(ix) FEATURE:
    (A) NAME/KEY: mat_peptide
    (B) LOCATION: 123..998

(xi) SEQUENCE DESCRIPTION: SEQ ID NO:14:

```
GGCACGAGGA GAGAGAGAGA GAGAGAACTA GTCTCGAGCA TCAAAGTACT CAAATTAGC          59

ATG GCT GTC ATG GTT GCA TTC TTG AAT TTG ATC ATC TTT TCA GTA GTC         107
Met Ala Val Met Val Ala Phe Leu Asn Leu Ile Ile Phe Ser Val Val
-21 -20              -15                  -10

TCT ACA ACA GGC AAG TCA CTG AGC TTA AAC TAC TAT GCA AAA ACA TGC         155
Ser Thr Thr Gly Lys Ser Leu Ser Leu Asn Tyr Tyr Ala Lys Thr Cys
 -5              1                   5                  10

CCT AAT GTG GAG TTC ATT GTT GCC AAG GCA GTA AAG GAT GCC ACT GCT         203
Pro Asn Val Glu Phe Ile Val Ala Lys Ala Val Lys Asp Ala Thr Ala
             15                  20                  25

AGG GAC AAA ACT GTT CCA GCA GCA ATT CTG CGA ATG CAC TTC CAT GAT         251
Arg Asp Lys Thr Val Pro Ala Ala Ile Leu Arg Met His Phe His Asp
         30                  35                  40

TGT TTC GTT CGG GGG TGT GAT GCC TCT GTG CTG CTA AAT TCA AAA GGA         299
Cys Phe Val Arg Gly Cys Asp Ala Ser Val Leu Leu Asn Ser Lys Gly
     45                  50                  55

AAC AAC AAA GCA GAA AAA GAC GGG CCA CCA AAT GTT TCT TTG CAT GCA         347
Asn Asn Lys Ala Glu Lys Asp Gly Pro Pro Asn Val Ser Leu His Ala
 60                  65                  70                  75

TTC TAT GTC ATT GTA GCA GCA AAG AAA GCA CTA GAA GCT TCA TGC CCT         395
Phe Tyr Val Ile Val Ala Ala Lys Lys Ala Leu Glu Ala Ser Cys Pro
                 80                  85                  90

GGT GTG GTC TCT TGT GCT GAC ATC CTT GCT CTG GCA GCA AGG GTC GCA         443
Gly Val Val Ser Cys Ala Asp Ile Leu Ala Leu Ala Ala Arg Val Ala
             95                 100                 105

GTT TTT CTG TCA GGA GGA CCT ACA TGG GAT GTT CCT AAA GGA AGA AAG         491
Val Phe Leu Ser Gly Gly Pro Thr Trp Asp Val Pro Lys Gly Arg Lys
         110                 115                 120

GAT GGT AGA ACA TCT AAA GCC AGT GAA ACC AGA CAA TTG CCA GCA CCA         539
Asp Gly Arg Thr Ser Lys Ala Ser Glu Thr Arg Gln Leu Pro Ala Pro
     125                 130                 135

ACC TTC AAC TTA TCA CAA CTG CGG CAA AGT TTC TCT CAA AGA GGA CTG         587
Thr Phe Asn Leu Ser Gln Leu Arg Gln Ser Phe Ser Gln Arg Gly Leu
140                 145                 150                 155

TCA GGG GAA GAC CTG GTA GCT CTG TCA GGG GGG CAC ACT TTG GGT TTC         635
Ser Gly Glu Asp Leu Val Ala Leu Ser Gly Gly His Thr Leu Gly Phe
                 160                 165                 170

TCT CAC TGC TCA TCT TTC AAG AAC AGA ATC CAC AAC TTC AAT GCA ACA         683
Ser His Cys Ser Ser Phe Lys Asn Arg Ile His Asn Phe Asn Ala Thr
             175                 180                 185
```

| | | | | | | | | | | | | | | | | |
|---|---|---|---|---|---|---|---|---|---|---|---|---|---|---|---|---|
|CAT|GAT|GTT|GAC|CCT|TCA|TTA|AAT|CCA|TCA|TTT|GCA|GCA|AAA|CTG|ATC|731|
|His|Asp|Val|Asp|Pro|Ser|Leu|Asn|Pro|Ser|Phe|Ala|Ala|Lys|Leu|Ile||
| |190| | | |195| | | | | |200| | | | | |
|TCA|ATT|TGT|CCA|CTA|AAA|AAT|CAG|GCA|AAA|AAT|GCA|GGC|ACC|TCT|ATG|779|
|Ser|Ile|Cys|Pro|Leu|Lys|Asn|Gln|Ala|Lys|Asn|Ala|Gly|Thr|Ser|Met||
| |205| | | |210| | | | |215| | | | | | |
|GAC|CCT|TCA|ACA|ACA|ACT|TTT|GAT|AAT|ACA|TAT|TAC|AGG|TTG|ATC|CTC|827|
|Asp|Pro|Ser|Thr|Thr|Thr|Phe|Asp|Asn|Thr|Tyr|Tyr|Arg|Leu|Ile|Leu||
|220| | | | |225| | | | |230| | | | |235| |
|CAA|CAG|AAA|GGC|TTG|TTT|TCT|TCT|GAT|CAA|GTT|TTG|CTT|GAC|AAC|CCA|875|
|Gln|Gln|Lys|Gly|Leu|Phe|Ser|Ser|Asp|Gln|Val|Leu|Leu|Asp|Asn|Pro||
| | | | |240| | | |245| | | | |250| | | |
|GAC|ACT|AAA|AAT|CTG|GTT|ACA|AAG|TTT|GCC|ACC|TCA|AAA|AAG|GCT|TTT|923|
|Asp|Thr|Lys|Asn|Leu|Val|Thr|Lys|Phe|Ala|Thr|Ser|Lys|Lys|Ala|Phe||
| | | |255| | | |260| | | | |265| | | | |
|TAT|GAG|GCT|TTT|GCG|AAG|TCC|ATG|ATC|AGA|ATG|AGT|AGC|TAC|AAT|GGT|971|
|Tyr|Glu|Ala|Phe|Ala|Lys|Ser|Met|Ile|Arg|Met|Ser|Ser|Tyr|Asn|Gly||
| | |270| | | |275| | | | |280| | | | | |
|GGA|CAG|GAG|GTT|AGA|AGG|ACT|GCA|GAA|TGATCAATTA|ATAAGTCTTA| | | | |1018|
|Gly|Gln|Glu|Val|Arg|Arg|Thr|Ala|Glu| | | | | | | | |
| |285| | | | |290| | | | | | | | | | |

AATCAATTCA AGTTAAATTG ATGTTCCAAA CAAGTTGGAT CAAATTTCCT AGATGCCAAG 1078

ATATTATGTC TTTTTCCTCT ATTAAAGAAA TATGTATATT TATCTGAAGT TAATAAAATC 1138

TCAAGCATGT CTTGGGAAAT TAATTTAGAG CTCAAAAAAA AAAAAAAAA AAA 1191

( 2 ) INFORMATION FOR SEQ ID NO:15:

( i ) SEQUENCE CHARACTERISTICS:
        ( A ) LENGTH: 313 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

| | | | | | | | | | | | | | | |
|---|---|---|---|---|---|---|---|---|---|---|---|---|---|---|
|Met|Ala|Val|Met|Val|Ala|Phe|Leu|Asn|Leu|Ile|Ile|Phe|Ser|Val|Val|
|-21| |-20| | | |-15| | | |-10| | | | | |
|Ser|Thr|Thr|Gly|Lys|Ser|Leu|Ser|Leu|Asn|Tyr|Tyr|Ala|Lys|Thr|Cys|
|-5| | | | |1| | | |5| | | | |10| |
|Pro|Asn|Val|Glu|Phe|Ile|Val|Ala|Lys|Ala|Val|Lys|Asp|Ala|Thr|Ala|
| | | |15| | | | |20| | | | |25| | |
|Arg|Asp|Lys|Thr|Val|Pro|Ala|Ala|Ile|Leu|Arg|Met|His|Phe|His|Asp|
| | | |30| | | | |35| | | | |40| | |
|Cys|Phe|Val|Arg|Gly|Cys|Asp|Ala|Ser|Val|Leu|Leu|Asn|Ser|Lys|Gly|
| | |45| | | | |50| | | | |55| | | |
|Asn|Asn|Lys|Ala|Glu|Lys|Asp|Gly|Pro|Pro|Asn|Val|Ser|Leu|His|Ala|
|60| | | | |65| | | | |70| | | | |75|
|Phe|Tyr|Val|Ile|Val|Ala|Ala|Lys|Lys|Ala|Leu|Glu|Ala|Ser|Cys|Pro|
| | | | |80| | | | |85| | | | |90| |
|Gly|Val|Val|Ser|Cys|Ala|Asp|Ile|Leu|Ala|Leu|Ala|Ala|Arg|Val|Ala|
| | | | |95| | | |100| | | | |105| | |
|Val|Phe|Leu|Ser|Gly|Gly|Pro|Thr|Trp|Asp|Val|Pro|Lys|Gly|Arg|Lys|
| | | |110| | | | |115| | | | |120| | |
|Asp|Gly|Arg|Thr|Ser|Lys|Ala|Ser|Glu|Thr|Arg|Gln|Leu|Pro|Ala|Pro|
| |125| | | | |130| | | | |135| | | | |
|Thr|Phe|Asn|Leu|Ser|Gln|Leu|Arg|Gln|Ser|Phe|Ser|Gln|Arg|Gly|Leu|
|140| | | | |145| | | | |150| | | | |155|
|Ser|Gly|Glu|Asp|Leu|Val|Ala|Leu|Ser|Gly|Gly|His|Thr|Leu|Gly|Phe|

```
                           160                        165                        170
Ser  His  Cys  Ser  Ser  Phe  Lys  Asn  Arg  Ile  His  Asn  Phe  Asn  Ala  Thr
               175                      180                      185

His  Asp  Val  Asp  Pro  Ser  Leu  Asn  Pro  Ser  Phe  Ala  Ala  Lys  Leu  Ile
               190                      195                      200

Ser  Ile  Cys  Pro  Leu  Lys  Asn  Gln  Ala  Lys  Asn  Ala  Gly  Thr  Ser  Met
          205                      210                      215

Asp  Pro  Ser  Thr  Thr  Thr  Phe  Asp  Asn  Thr  Tyr  Tyr  Arg  Leu  Ile  Leu
220                           225                      230                      235

Gln  Gln  Lys  Gly  Leu  Phe  Ser  Ser  Asp  Gln  Val  Leu  Leu  Asp  Asn  Pro
                    240                      245                           250

Asp  Thr  Lys  Asn  Leu  Val  Thr  Lys  Phe  Ala  Thr  Ser  Lys  Lys  Ala  Phe
               255                      260                      265

Tyr  Glu  Ala  Phe  Ala  Lys  Ser  Met  Ile  Arg  Met  Ser  Ser  Tyr  Asn  Gly
          270                      275                      280

Gly  Gln  Glu  Val  Arg  Arg  Thr  Ala  Glu
          285                      290
```

( 2 ) INFORMATION FOR SEQ ID NO:16:

( i ) SEQUENCE CHARACTERISTICS:
        ( A ) LENGTH: 1167 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..38

( i x ) FEATURE:
        ( A ) NAME/KEY: CDS
        ( B ) LOCATION: 39..977

( i x ) FEATURE:
        ( A ) NAME/KEY: 3'UTR
        ( B ) LOCATION: 978..1167

( i x ) FEATURE:
        ( A ) NAME/KEY: sig_peptide
        ( B ) LOCATION: 39..101

( i x ) FEATURE:
        ( A ) NAME/KEY: mat_peptide
        ( B ) LOCATION: 102..977

( x i ) SEQUENCE DESCRIPTION: SEQ ID NO:16:

```
GGCACGAGGC  TAAAAATCAT  CGAAGTACTC  AAATTAGC  ATG  GCT  GTC  ATG  GTT              53
                                              Met  Ala  Val  Met  Val
                                              -21  -20

GCA  TTC  TTG  AAT  TTG  ATC  ATC  ATG  TTT  TCA  GTA  GTC  TCT  ACA  AGC  AAG   101
Ala  Phe  Leu  Asn  Leu  Ile  Ile  Met  Phe  Ser  Val  Val  Ser  Thr  Ser  Lys
     -15                      -10                      -5

TCA  CTG  AGC  TTA  AAC  TAC  TAT  TCA  AAA  ACA  TGC  CCT  GAT  GTG  GAA  TGC   149
Ser  Leu  Ser  Leu  Asn  Tyr  Tyr  Ser  Lys  Thr  Cys  Pro  Asp  Val  Glu  Cys
 1              5                      10                      15

ATT  GTT  GCC  AAG  GCA  GTG  AAG  GAT  GCC  ACT  GCT  AGG  GAC  AAA  ACT  GTT   197
Ile  Val  Ala  Lys  Ala  Val  Lys  Asp  Ala  Thr  Ala  Arg  Asp  Lys  Thr  Val
               20                      25                      30

CCA  GCT  GCA  CTT  CTG  CGA  ATG  CAC  TTC  CAT  GAC  TGT  TTC  GTT  CGG  GGG   245
Pro  Ala  Ala  Leu  Leu  Arg  Met  His  Phe  His  Asp  Cys  Phe  Val  Arg  Gly
          35                      40                      45

TGT  GGT  GCC  TCT  GTG  CTG  CTA  AAT  TCA  AAA  GGA  AGC  AAC  AAA  GCA  GAA   293
```

| | | | | | | | | | | | | | | | |
|---|---|---|---|---|---|---|---|---|---|---|---|---|---|---|---|
| Cys | Gly | Ala | Ser | Val | Leu | Leu | Asn | Ser | Lys | Gly | Ser | Asn | Lys | Ala | Glu |
| | | | 50 | | | 55 | | | | | 60 | | | | |

| AAA | GAT | GGG | CCA | CCA | AAT | GTT | TCT | TTG | CAT | GCA | TTC | TAT | GTC | ATT | GAT | 341 |
|---|---|---|---|---|---|---|---|---|---|---|---|---|---|---|---|---|
| Lys | Asp | Gly | Pro | Pro | Asn | Val | Ser | Leu | His | Ala | Phe | Tyr | Val | Ile | Asp | |
| 65 | | | | | 70 | | | | 75 | | | | | | 80 | |

| GCA | GCG | AAG | AAA | GCA | CTA | GAA | GCT | TCA | TGC | CCA | GGT | GTG | GTC | TCT | TGT | 389 |
|---|---|---|---|---|---|---|---|---|---|---|---|---|---|---|---|---|
| Ala | Ala | Lys | Lys | Ala | Leu | Glu | Ala | Ser | Cys | Pro | Gly | Val | Val | Ser | Cys | |
| | | | | 85 | | | | | 90 | | | | | 95 | | |

| GCT | GAC | ATC | CTT | GCT | CTA | GCA | GCA | AGG | GAT | GCA | GTT | TTT | CTG | TCA | GGA | 437 |
|---|---|---|---|---|---|---|---|---|---|---|---|---|---|---|---|---|
| Ala | Asp | Ile | Leu | Ala | Leu | Ala | Ala | Arg | Asp | Ala | Val | Phe | Leu | Ser | Gly | |
| | | | 100 | | | | | 105 | | | | | 110 | | | |

| GGA | CCT | ACA | TGG | GAT | GAA | CCT | AAA | GGA | AGA | AAG | GAT | GGC | AGA | ACA | TCT | 485 |
|---|---|---|---|---|---|---|---|---|---|---|---|---|---|---|---|---|
| Gly | Pro | Thr | Trp | Asp | Glu | Pro | Lys | Gly | Arg | Lys | Asp | Gly | Arg | Thr | Ser | |
| | | 115 | | | | | 120 | | | | | 125 | | | | |

| AAA | GCC | AGC | GAA | ACC | AGA | CAA | TTA | CCA | GCA | CCA | ACC | TTC | AAC | TTA | TCA | 533 |
|---|---|---|---|---|---|---|---|---|---|---|---|---|---|---|---|---|
| Lys | Ala | Ser | Glu | Thr | Arg | Gln | Leu | Pro | Ala | Pro | Thr | Phe | Asn | Leu | Ser | |
| 130 | | | | | 135 | | | | | 140 | | | | | | |

| CAA | CTG | CGG | CAA | AGC | TTT | TCT | CAA | AGA | GGA | CTG | TCA | GGG | GAA | GAC | CTG | 581 |
|---|---|---|---|---|---|---|---|---|---|---|---|---|---|---|---|---|
| Gln | Leu | Arg | Gln | Ser | Phe | Ser | Gln | Arg | Gly | Leu | Ser | Gly | Glu | Asp | Leu | |
| 145 | | | | | 150 | | | | | 155 | | | | | 160 | |

| GTA | GCT | CTG | TCA | GGG | GGG | CAC | ACT | TTG | GGT | TTC | TCT | CAC | TGC | TCA | TCT | 629 |
|---|---|---|---|---|---|---|---|---|---|---|---|---|---|---|---|---|
| Val | Ala | Leu | Ser | Gly | Gly | His | Thr | Leu | Gly | Phe | Ser | His | Cys | Ser | Ser | |
| | | | | 165 | | | | | 170 | | | | | 175 | | |

| TTC | AAG | AAC | AGA | ATC | CAC | AAC | TTC | AAT | GCT | ACA | CAT | GAT | GAA | GAC | CCT | 677 |
|---|---|---|---|---|---|---|---|---|---|---|---|---|---|---|---|---|
| Phe | Lys | Asn | Arg | Ile | His | Asn | Phe | Asn | Ala | Thr | His | Asp | Glu | Asp | Pro | |
| | | | 180 | | | | | 185 | | | | | 190 | | | |

| TCA | TTA | AAT | CCA | TCA | TTT | GCA | ACA | AAA | CTG | ATA | TCA | ATT | TGT | CCA | CTA | 725 |
|---|---|---|---|---|---|---|---|---|---|---|---|---|---|---|---|---|
| Ser | Leu | Asn | Pro | Ser | Phe | Ala | Thr | Lys | Leu | Ile | Ser | Ile | Cys | Pro | Leu | |
| | | 195 | | | | | 200 | | | | | 205 | | | | |

| AAA | AAT | CAG | GCA | AAA | AAT | GCA | GGC | ACC | TCT | ATG | GAC | CCT | TCA | ACA | ACA | 773 |
|---|---|---|---|---|---|---|---|---|---|---|---|---|---|---|---|---|
| Lys | Asn | Gln | Ala | Lys | Asn | Ala | Gly | Thr | Ser | Met | Asp | Pro | Ser | Thr | Thr | |
| | 210 | | | | | 215 | | | | | 220 | | | | | |

| ACT | TTT | GAT | AAT | ACA | TAT | TAC | AGG | TTG | ATC | CTC | CAA | CAG | AAA | GGC | TTG | 821 |
|---|---|---|---|---|---|---|---|---|---|---|---|---|---|---|---|---|
| Thr | Phe | Asp | Asn | Thr | Tyr | Tyr | Arg | Leu | Ile | Leu | Gln | Gln | Lys | Gly | Leu | |
| 225 | | | | | 230 | | | | | 235 | | | | | 240 | |

| TTT | TCT | TCT | GAT | CAA | GTT | TTG | CTT | GAC | AAC | CCA | GAC | ACT | AAA | AAT | CTG | 869 |
|---|---|---|---|---|---|---|---|---|---|---|---|---|---|---|---|---|
| Phe | Ser | Ser | Asp | Gln | Val | Leu | Leu | Asp | Asn | Pro | Asp | Thr | Lys | Asn | Leu | |
| | | | | 245 | | | | | 250 | | | | | 255 | | |

| GTT | GCG | AAG | TTT | GCC | ACC | TCA | AAA | AAG | GCT | TTT | TAT | GAC | GCT | TTT | GCA | 917 |
|---|---|---|---|---|---|---|---|---|---|---|---|---|---|---|---|---|
| Val | Ala | Lys | Phe | Ala | Thr | Ser | Lys | Lys | Ala | Phe | Tyr | Asp | Ala | Phe | Ala | |
| | | | 260 | | | | | 265 | | | | | 270 | | | |

| AAG | TCC | ATG | ATC | AAA | ATG | AGT | AGC | ATC | AAT | GGT | GGA | CAG | GAG | GTT | AGA | 965 |
|---|---|---|---|---|---|---|---|---|---|---|---|---|---|---|---|---|
| Lys | Ser | Met | Ile | Lys | Met | Ser | Ser | Ile | Asn | Gly | Gly | Gln | Glu | Val | Arg | |
| | | 275 | | | | | 280 | | | | | 285 | | | | |

| AGG | ACT | GCA | GAG | TGATCAATTA | AAAAGTCTTA | AATTAATTCA | AGTTAAATTG | | | | | | | | | 1017 |
|---|---|---|---|---|---|---|---|---|---|---|---|---|---|---|---|---|
| Arg | Thr | Ala | Glu | | | | | | | | | | | | | |
| | 290 | | | | | | | | | | | | | | | |

ATGTTTCAAA CAAGTTAGAA GTATGAACTT GTTGGATCAA ATTTCCTAGA TGGCAAGATA 1077

TTATGTCTTT TTCCTCTATT AAAGAAATAT GTATATTTAT CTGAAGTTAA TAAATATATC 1137

ATTTTGATAA AAAAAAAAAA AAAAAAAAA 1167

( 2 ) INFORMATION FOR SEQ ID NO:17:

( i ) SEQUENCE CHARACTERISTICS:
        ( A ) LENGTH: 313 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met  Ala  Val  Met  Val  Ala  Phe  Leu  Asn  Leu  Ile  Ile  Met  Phe  Ser  Val
-21  -20                      -15                      -10

Val  Ser  Thr  Ser  Lys  Ser  Leu  Ser  Leu  Asn  Tyr  Tyr  Ser  Lys  Thr  Cys
-5                        1                    5                         10

Pro  Asp  Val  Glu  Cys  Ile  Val  Ala  Lys  Ala  Val  Lys  Asp  Ala  Thr  Ala
               15                       20                        25

Arg  Asp  Lys  Thr  Val  Pro  Ala  Ala  Leu  Leu  Arg  Met  His  Phe  His  Asp
               30                       35                   40

Cys  Phe  Val  Arg  Gly  Cys  Gly  Ala  Ser  Val  Leu  Leu  Asn  Ser  Lys  Gly
     45                       50                        55

Ser  Asn  Lys  Ala  Glu  Lys  Asp  Gly  Pro  Pro  Asn  Val  Ser  Leu  His  Ala
60                       65                       70                              75

Phe  Tyr  Val  Ile  Asp  Ala  Ala  Lys  Lys  Ala  Leu  Glu  Ala  Ser  Cys  Pro
               80                       85                              90

Gly  Val  Val  Ser  Cys  Ala  Asp  Ile  Leu  Ala  Leu  Ala  Ala  Arg  Asp  Ala
               95                      100                       105

Val  Phe  Leu  Ser  Gly  Gly  Pro  Thr  Trp  Asp  Glu  Pro  Lys  Gly  Arg  Lys
          110                      115                       120

Asp  Gly  Arg  Thr  Ser  Lys  Ala  Ser  Glu  Thr  Arg  Gln  Leu  Pro  Ala  Pro
     125                      130                       135

Thr  Phe  Asn  Leu  Ser  Gln  Leu  Arg  Gln  Ser  Phe  Ser  Gln  Arg  Gly  Leu
140                           145                      150                          155

Ser  Gly  Glu  Asp  Leu  Val  Ala  Leu  Ser  Gly  Gly  His  Thr  Leu  Gly  Phe
                    160                           165                     170

Ser  His  Cys  Ser  Ser  Phe  Lys  Asn  Arg  Ile  His  Asn  Phe  Asn  Ala  Thr
               175                      180                       185

His  Asp  Glu  Asp  Pro  Ser  Leu  Asn  Pro  Ser  Phe  Ala  Thr  Lys  Leu  Ile
          190                      195                       200

Ser  Ile  Cys  Pro  Leu  Lys  Asn  Gln  Ala  Lys  Asn  Ala  Gly  Thr  Ser  Met
     205                      210                       215

Asp  Pro  Ser  Thr  Thr  Thr  Phe  Asp  Asn  Thr  Tyr  Tyr  Arg  Leu  Ile  Leu
220                      225                       230                           235

Gln  Gln  Lys  Gly  Leu  Phe  Ser  Ser  Asp  Gln  Val  Leu  Leu  Asp  Asn  Pro
               240                      245                            250

Asp  Thr  Lys  Asn  Leu  Val  Ala  Lys  Phe  Ala  Thr  Ser  Lys  Lys  Ala  Phe
               255                      260                       265

Tyr  Asp  Ala  Phe  Ala  Lys  Ser  Met  Ile  Lys  Met  Ser  Ser  Ile  Asn  Gly
          270                      275                       280

Gly  Gln  Glu  Val  Arg  Arg  Thr  Ala  Glu
     285                      290
```

SOYBEAN PEROXIDASE GENE FAMILY AND AN ASSAY FOR DETECTING SOYBEAN PEROXIDASE ACTIVITY

BACKGROUND OF THE INVENTION

The present invention relates to the DNA sequences of the soybean peroxidase, and to the enzymatic assay of peroxidase activity. The invention further relates to medical and environmental diagnostics employing soybean peroxidase monoclonal antibody in place of horseradish peroxidase polyclonal antibodies which has been historically used.

Peroxidase is a class of proteins whose primary function is to oxidize a variety of hydrogen donors at the expense of peroxide or molecular oxygen. Areas where peroxidase could have an immediate use are: pulp and paper bleaching; on-site waste destruction; soil remediation; organic synthesis; and diagnostic chemistries.

At present, pulp and paper is bleached using chloride ions as a chemical agent. Soybean peroxidase has several advantages over chlorine bleach: lower cost; environmentally friendly; and hydroxyl ions produced by peroxidase have twice the oxidation power of chlorine ions.

In waste water and soil treatments, peroxidase has advantages since many organic compounds are toxic, inhibitory, or refractory to microbes, and certain organic compounds may result in the production of microbial products that produce toxic or offensive effluent.

The use of oxidation to achieve on-site destruction or detoxification of contaminated water and waste will increase in the future. If carried out to its ultimate stage, oxidation can completely oxidize organic compounds to carbon dioxide, water and salts.

Peroxidase has several uses in organic synthesis. Using peroxidase, researchers synthesized conductive polyaniline that produced only water as a by-product. Peroxidase can also be used in the manufacturing of adhesive and antioxidant intermediates.

Enzymes are now widely used in medical and environmental diagnostics. Horseradish peroxidase has been one of the most satisfactory enzymes but is relatively expensive. It has now been found that soybean peroxidase can be readily harvested from soybean hulls at minimal expense and be substituted for horseradish peroxidase in these diagnostic chemistries.

Several diagnostic chemistries using the enzymatic activity of horseradish peroxidase and polyclonal antibodies have been described in the literature. Horseradish peroxidase has been used for diagnostic determinations of various analytes and has been used as a label in enzyme labeled antibodies used in the determination of immunologically reactive species (i.e., immunoassays). Such determinations can be carried out in solution or in dry analytical elements.

One type of useful assay utilizes enzymatic reactions wherein the analyte, upon contact with the appropriate reagents, reacts with oxygen in the presence of a suitable enzyme to produce hydrogen peroxide in proportion to the concentration of the analyte. A detectable product such as a visible or fluorescent dye is then produced by the reaction of hydrogen peroxide in proportion to the concentration of the analyte in the tested liquids. Peroxidase is generally used in such assays to catalyze the oxidation of the interactive composition by hydrogen peroxide. One example of such an assay is a glucose assay using glucose oxidase. Glucose is oxidized in the presence of oxygen by the enzyme, glucose oxidase, to produce glucolactone and hydrogen peroxide. In the presence of peroxidase, the hydrogen peroxide oxidizes a colorless dye such as tetramethylbenzidine to produce a colored product.

Another type of assay utilizes an immunologically reactive compound such as an antibody. These chemistries can be generally classified into two groups, namely, conjugate or enzyme labeled antibody procedures, and non-conjugate or unlabeled antibody procedures. In the conjugate procedures, the enzyme is covalently linked to the antibody and applied to a sample containing the immobilized antigen to be detected. Thereafter the enzyme substrate, e.g., hydrogen peroxide, and an oxidizable chromogen such as a leuco dye are applied. In the presence of the peroxidase, the peroxide reacts with the chromogen resulting in the production of color. The production of color indicates the presence and in some cases the amount of the antigen. In another method, a competing substance is used to dislodge an antibody enzyme conjugate from an immobilized substrate, leading to an absence of color.

In a method sometimes referred to as the sandwich assay or enzyme linked immunoadsorbent assay (ELISA), a first antibody is bound to a solid support surface and contacted with a fluid sample suspected to contain the antigen to be detected and an enzyme-antibody conjugate. The antigen complexes with the antibody and the conjugate bonds to the antigen. Subsequent introduction of the substrate and chromogen produces a visual indication of the presence of the antigen.

Procedures employing non-conjugated enzymes include the enzyme bridge method and the peroxidase-antiperoxidase method. These methods use an antiperoxidase antibody produced by injecting peroxidase into an animal such as a goat, rabbit or guinea pig. The method does not require chemical conjugation of the antibody to the enzyme but consists of binding the enzyme to the antigen through the antigen-antibody reaction of an immunoglobulin-enzyme bridge. In the enzyme bridge method a secondary antibody acts as an immunologic bridge between the primary antibody against the suspected antigen and the antiperoxidase antibody. The antiperoxidase antibody in turn binds the peroxidase which catalyzes the indicator reaction. In the peroxidase-antiperoxidase method, a complex of the peroxidase and the antiperoxidase antibody is formed. This complex can then be used in the immunologic bridge method.

Though peroxidase genes from different biologic sources have been identified, including other plant peroxidase genes from horseradish, tomato, pea, arabidopsis, peanut and turnip, and bacterial lignin peroxidase gene, there have not been any reports regarding identification of peroxidase genes from soybean.

Soybean coats are abundant and inexpensive, making them an excellent source of peroxidase. Therefore, there is substantial interest in cloning soybean peroxidase genes which will open the possibility of characterization of the expression patterns of individual peroxidase isoforms during normal plant development and genetic and molecular manipulations for increased peroxidase activity.

BRIEF DESCRIPTION OF THE DRAWINGS

FIG. 5A and 5B Comparisons of nucleotide sequences of the coding regions of the SEPa1 and SEPa2 genes and the predicted amino acid sequences of SEPa1 (p1) and SEPa2 (p2). Amino acid sequences are shown using the single-letter code. The complete coding and predicted amino acid sequences are given only for SEPa1 (first and third lines, respectively). To emphasize the similarity between the two genes and their products, only those nucleotides in the coding region of SEPa2 and the predicted amino acid that differ from the corresponding ones in SEPa1 and p1are shown. The dots indicate identity of nucleotides and amino acids. For example, a dot under a nucleotide represents the presence of the same nucleotide that is directly above the dot. The signal peptide is shown in bold italics. The start of the mature proteins begins with the [QLXXXFY] motif at position 1. The cysteine residues in disulfide bridges are shaded. Conserved amino acid areas are outlines.

FIG. 6A and 6B Comparisons of the nucleotide sequences of the coding regions of the SEPb1 and SEPb2 genes and the predicted amino acid sequences of SEPb1 (p3) and SEPb2 (p4). Amino acid sequences are shown using the single-letter code. The complete coding and predicted amino acid sequences are given only for SEPb1 (first and third lines, respectively). The dots indicate identity of nucleotides and amino acids. The asterisks indicate the gap of nucleotides and amino acids between SEPb1 and SEPb2, p3 and p3, respectively. The cysteine residues are shaded and the conserved amino acid areas are outlines. For example, a dot under a nucleotide represents the presence of the same nucleotide that is directly above the dot. The signal peptide is shown in bold italics.

SUMMARY OF THE INVENTION

Figure 1:
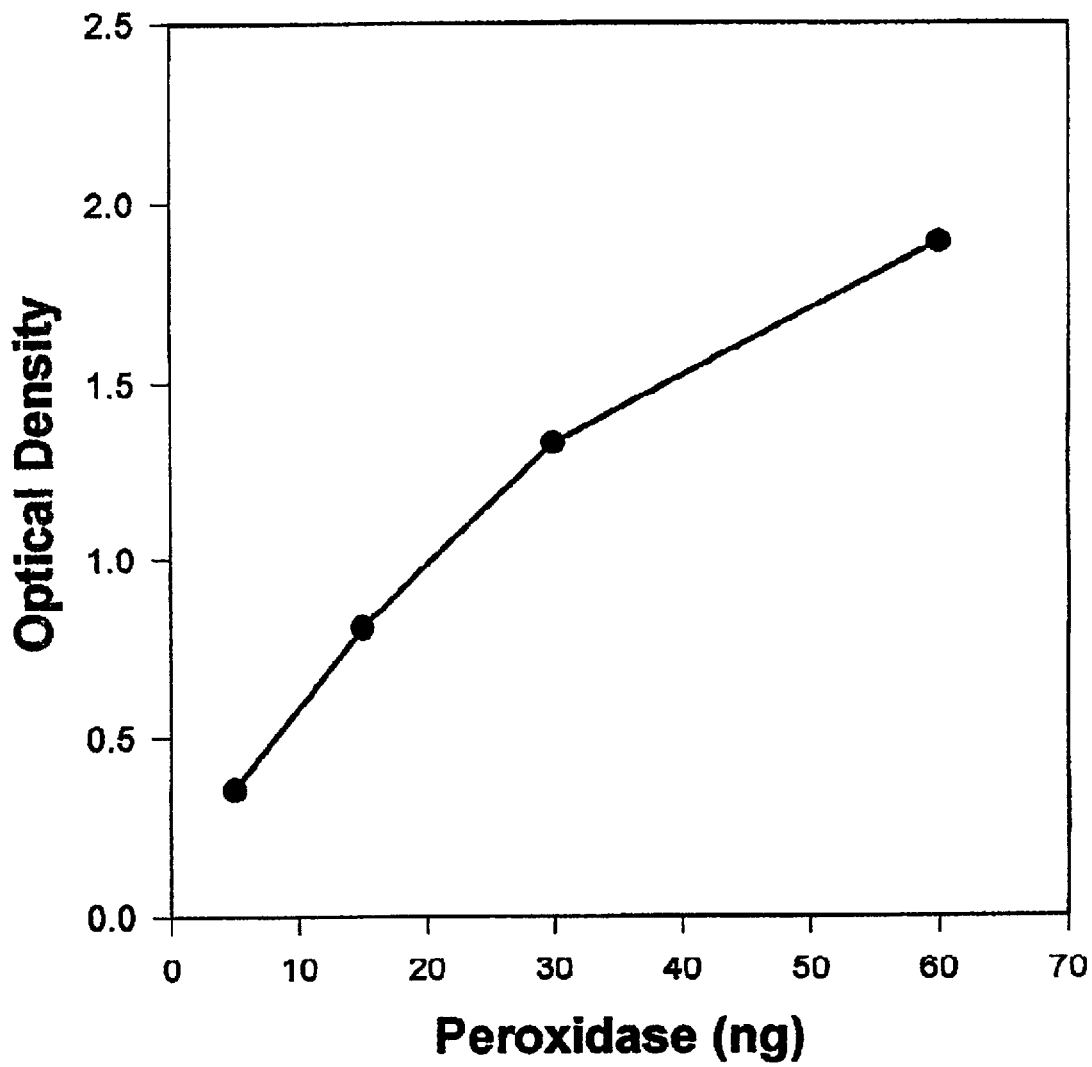
FIG. 1 Average ELISA absorbance (405 nm) of purified peroxidase samples against 1:10 dilution of peroxidase monoclonal antibodies (MAB).

The present invention relates to a method for quantifying plant peroxidase activity by using a monoclonal antibody against peroxidase.

The method of the present invention further allows a direct quantitative assay of peroxidase activity in biological materials and in solutions containing peroxidase.

Additionally, the method of the present invention can be used to identify differences in peroxidase activity between plant genotypes within a segregating population of genotypes, as in a plant breeding research field, grain elevator or processing plant. Therefore, the method of the instant invention can be used to easily find and select for plants having improved levels of peroxidase activity. The invention is non-destructive to seed or plants. Cultivars selected using the method of the present invention increase the sensitivity of diagnostic applications and reduces the cost of enzyme purification.

The present invention further involves four DNA sequences representing a soybean peroxidase gene family. These DNA sequences of the present invention encode amino acids that show homology to other plant peroxidase conserved amino acid regions. Outside the conserved regions the sequences show a high degree of divergence from other plant peroxidases.

The amino acid sequences of the present invention further contain hydrophobic signal peptides at their N-termini and mature proteins can be secreted through all membranes.

The present invention further relates to using tetramethylbenzadine as a substrate, a simple linear model quantifies the relation between peroxidase activity and peroxidase quantity where the slope indicates the specific activity.

The method of the present invention further relates to a direct method without the secondary enzyme-linked antibody as used in reaction found in ELISA.

The invention also relates to a kit for measuring peroxidase activity outside the laboratory to determine the effect of environment and seed storage on peroxidase activity, and allows direct selection of high peroxidase genotypes in a plant breeding field, grain elevator and processing plant. The kit also allows quantitation and monitoring of peroxidase activity in processes using peroxidase or peroxidase solutions, such as pulp and paper bleaching, on-site waste destruction, soil remediation and organic synthesis.

The present invention also relates to an antiperoxidase antibody which does not inhibit peroxidase activity which can be used in the following: enzyme capture assay for activity quantification; ELISA for peroxidase concentration; soybean peroxidase capture assay (SPCA) kits for measuring activity outside the lab; ELISA kits for measuring concentration outside the lab; peroxidase-antiperoxidase conjugates; immunohistochemical detection; immunoperoxidase microscopy and immunopurification of peroxidase.

The peroxidase-antiperoxidase conjugates of the present invention are useful in the following applications: non-radioactive nucleic acid labeling and detection; conjugating antibody complex in western blot; ELISA reactions; ELISA detection of DNA and RNA; and conjugate to polymerase chain reaction (PCR) products.

DETAILED DESCRIPTION OF THE INVENTION

In order to provide an understanding of several of the terms used in the specification and claims, the following definitions are provided:

"Operably linked"—The term operably linked refers to a juxtaposition wherein the components so described are in a relationship permitting them to function in their intended manner, i.e., a promoter is operably linked to a coding sequence if the promoter affects its transcription or expression.

"Isolated", "substantially pure" and "substantially homogeneous"—These terms are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95% w/w, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art for purification utilized.

A MTS protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Nondestructive"—The term nondestructive refers to the ability of quantitating peroxidase activity without killing the seed, plant or rendering peroxidase non-enzymatically active.

The present invention is directed to a method of quantitating peroxidase activity, a kit for quantitating peroxidase activity, immunological assays, and DNA sequences regulating and representing a soybean peroxidase gene family.

The method of this invention is adaptable to both solution and dry assays and describes the capture of peroxidase by an antibody from a solution. Antibodies are immobilized on a solid support and unbound matrix is blocked with unreactive proteins. Solutions containing peroxidase are incubated with the immobilized antibodies and then removed. Captured peroxidase is then assayed for activity with any substrate, with or without additives, previously used in horseradish peroxidase assays. This invention does not use a secondary enzyme-linked antibody like an ELISA assay.

The method of this invention can also be practiced with a dry analytical element. The kit may be composed of an absorbent carrier material, e.g. a thin sheet of a self-supporting absorbent or bibulous material, such as filter paper or strips, which contains an immobilized antibody. The element can be divided into multiple zones with different compositions of the antibody incorporated into individual zones of the carrier material. Such elements are known as test strips, diagnostic elements, dip sticks, diagnostic agents and the like.

The assay or test kit can be used to quantitate peroxidase activity in plant fluids from macerated tissue with or without exogenous liquid added. Such fluids include, but are not limited to, fluids from leaves, stems, roots, flowers, seeds, seed coats, embryos, hypocotyls, coleoptiles, seed pods and seed buds. It is also possible to assay fluids from a variety of plant species including, but not limited to, soybean, corn, wheat, sorghum and oats.

This invention allows for the selection of high peroxidase plant genotypes in the field of plant breeding. Since minimal amounts of tissue are needed, unlike other methods of assaying peroxidase activity, e.g. Gilliken and Graham, Plant Physiol. 96:214–220 (1991), this invention is non-destructive to the seed or resulting plant. This greatly accelerates the progress of plant breeding for high peroxidase levels. The non-destructive nature allows high peroxidase plant genotypes to be selected and advanced to the next generation. The non-destructive nature of the assay is unique. In addition to the non-destructive nature of the assay, another unique trait of the present invention is the quantitative nature of the assay. Being quantitative, the present invention allows for the ultimate discriminatory assay for the separation of high peroxidase genotypes. Previous assays are not able to separate high peroxidase genotypes, e.g. Buttery & Buzzell, Crop Science 8:722–725 (1968). The ranking of high peroxidase genotypes, based on activity, will allow for the most efficient selection for high peroxidase genotypes. This invention is unique in that it is the only method that is non-destructive to the seed or plant and also is quantitative.

The assay or kit can be used to monitor peroxidase activity in industrial processes and is an identity preserved system to deliver high peroxidase plant material to processors. In an identity preserved system, kits will be used to identify high peroxidase seeds or to monitor activity from the seed company, to the farmer's field, grain elevator, grain truck and finally to the processing facility. The kit also can be used to monitor peroxidase activity in stored peroxidase solutions. In industrial processes that use peroxidase, the kit can be used to monitor peroxidase activity.

The invention also can be used to determine antigens using an enzyme- antibody conjugate method. In this embodiment, the enzyme label can be any plant peroxidase that participates in the conversion of a chromogen or luminal to a detectable form.

Other uses of the present invention involve the modification of the peroxidase enzyme, the peroxidase gene or bacteria containing the enzyme. The entire gene with its 5'- and 3'- regulatory regions can be manipulated in a variety of ways to provide for expression and enzyme form.

In general, expression can be enhanced by including multiple copies of the peroxidase gene in a transformed bacterial or plant host, by using promoters that initiate transcription at increased levels, or by any known means of enhancing peptide expressions.

A recombinant gene can be constructed that takes advantage of regulatory regions from other genes and the coding region of the peroxidase genes. Alternatively, a recombinant gene can be constructed that takes advantage of the peroxidase regulatory regions and coding regions from other genes.

EXAMPLES

The following examples are provided to further illustrate the present invention and are not intended to limit the invention beyond the limitations set forth in the appended claims.

EXAMPLE 1

Peroxidase Extraction and Monoclonal Antibody Production

Peroxidase was extracted from circular pieces of seed coat, roughly 3 mm in diameter. Samples from three seeds per replication were placed separately in micro centrifuge tubes containing 1 ml of water, incubated at room temperature for 2 hours and vortexed.

Purified seed coat peroxidase (>95% pure) and seed coat peroxidase solutions with various levels of known pupurogallin (PPU) activity were kindly provided by Enzymol International (Columbus, Ohio).

Seeds of high and low peroxidase cultivars were grown at the Purdue Agronomy Farm at West Lafayette, and a Resnik x Winchester cross was made during the summer of 1993. $F_1$ seeds were grown in Puerto Rico, $F_2$ seeds were grown in West Lafayette and $F_3$ individual seeds were tested for peroxidase activity.

BALB/c mice (Mus musculus) were subcutaneously injected with a total of 0.1 mg purified seed coat peroxidase (>95% pure) kindly provided by Mead Central Research (Chillicothe, Ohio). Fusions with myeloma parent P3/NS1/1-Ag4-1 (NS-1) were done with polyethylene glycol 4000. Hybridomas were selected on hypoxanthine (100 nM), aminopterin (0.4 nM), and thymidine (16 nM) media and clones were obtained using the limited dilution method. Raw ascites solution was collected and used in all procedures. Hybridomas were initially selected on their antibody's ability to bind peroxidase. Hybridomas were subsequently selected on their antibody's ability to bind peroxidase in such a way as to not affect enzymatic ability. We have selected a hybridoma that has been designated A4.

EXAMPLE 2

Enzyme-linked Immunosorbent Assay (ELISA)

An indirect detection method using an alkaline phosphatase antimouse immunoglobulin and p-nitrophenyl phosphate as the chromogen was used to detect seed coat peroxidase. Raw ascites was diluted 1:10, 1:100, 1:1000, and 1:5000. Quantitation of three wells per replication was done at 405 nm after 45 minutes of development. ELISA detects protein or enzyme concentration but not enzyme activity, so ELISA is not suitable for plant breeding for higher peroxidase activity, or the detection or monitoring of peroxidase activity (FIG. 1).

EXAMPLE 3

Peroxidase Capture Assay (PCA)

Figure 2:
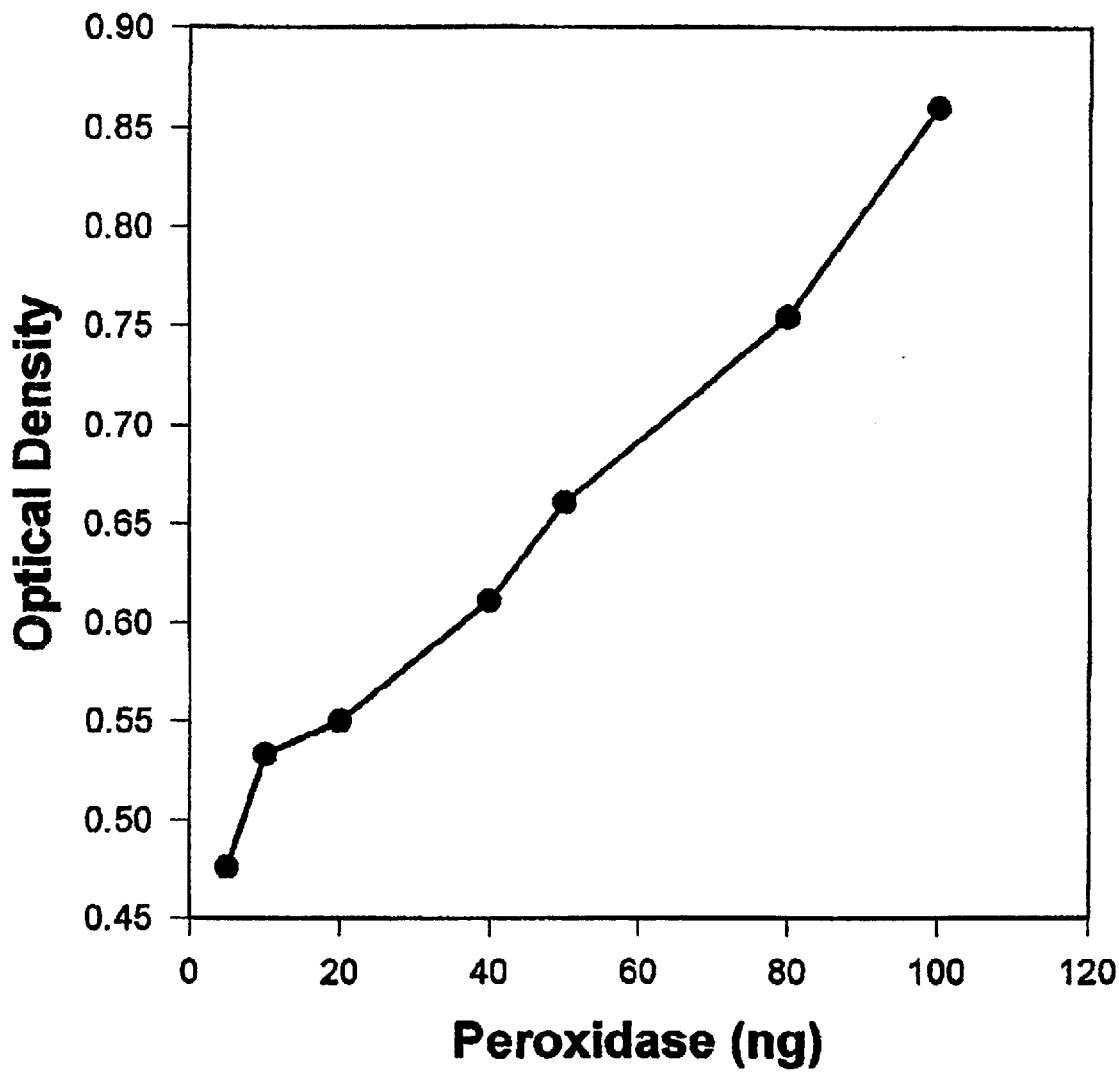
FIG. 2 Average Peroxidase Capture Assay (PCA absorbance (450 nm) of purified peroxidase samples against 1:5000 dilution of peroxidase MAB.

ELISA plate wells were coated with 100 $\mu$L of a 1:100, 1:1000, 1:5000, and 1:10,000 dilution of ascites fluid and incubated overnight at 4° C. After incubation, the ascites fluid was removed and 100$\mu$L of 1% (w/v) bovine serum albumin, acting as a blocking agent, was added. After a 1-h incubation at room temperature, wells were washed three times with phosphate-buffered saline (PBS; 137 mM NaCl, 1.47 mM $KH_2PO_4$, 8.10 mM $Na_2HPO_4$, and 2.68 mM KCl, pH 7.4) containing 0.05% (v/v) Tween-20. Peroxidase samples were added to the wells and incubated at room temperature for 1 h. Wells were washed three times with PBS-Tween-20. A soluble, peroxidase chromogenic substrate (100 $\mu$L, tetramethylbenzadine) was added to the bound peroxidase. After 30 seconds, the reactions were stopped by the addition of 50 $\mu$L of 1N $H_2SO_4$ and three wells per replication were read at 450 nm (FIG. 2).

EXAMPLE 4

Guaiacol Method

Figure 3:
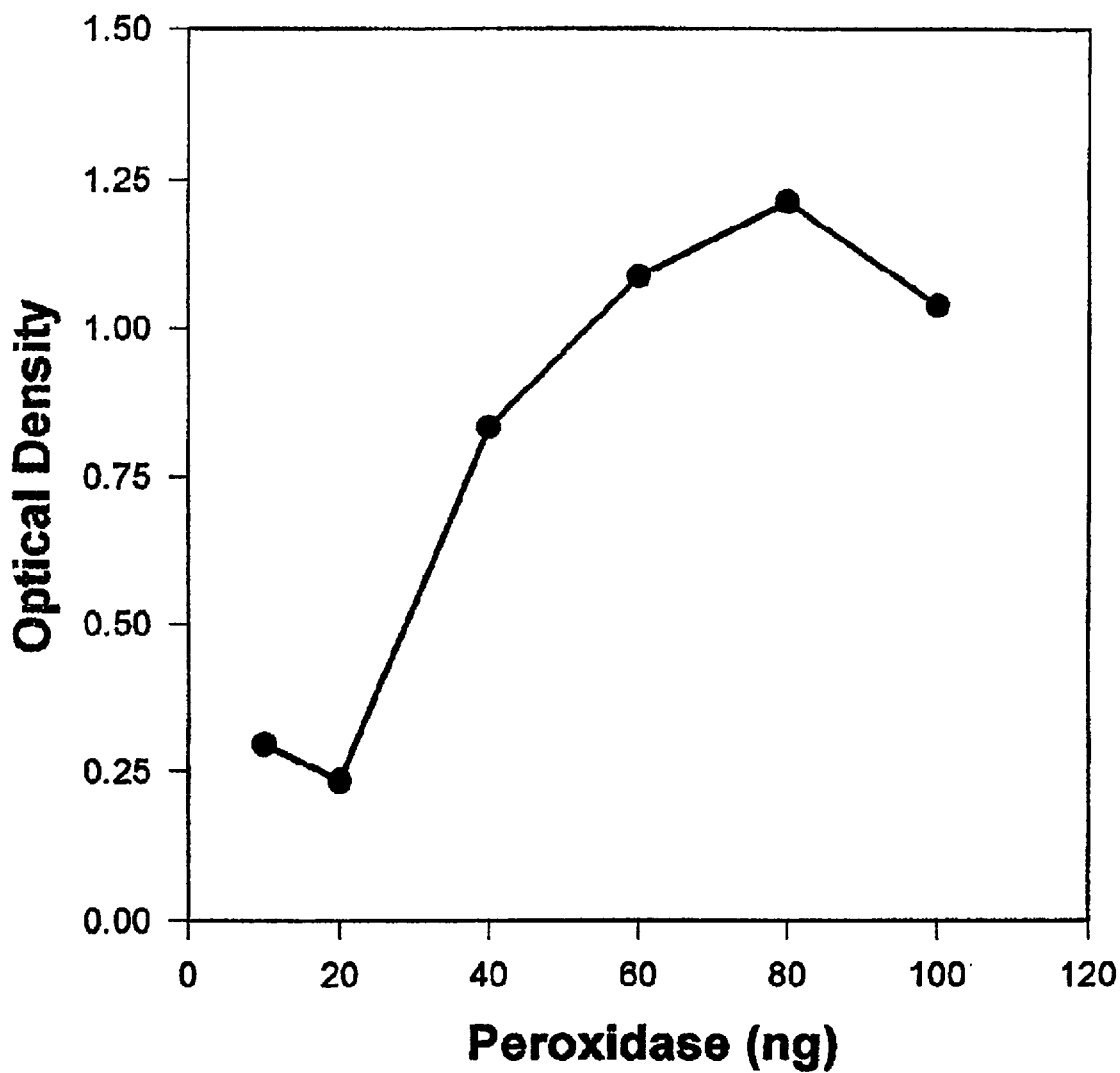
FIG. 3 Average guaiacol absorbance (470 nm) of purified peroxidase.

Purified peroxidase or seed coats were incubated in micro centrifuge tubes containing 1 ml of 0.5% (v/v) guaiacol at room temperature for 10 minutes before the addition of 50 $\mu$L of 0.1% (v/v) hydrogen peroxide. After 5 minutes, peroxidase activity was noted, with a brown solution being positive and a clear solution being negative. Peroxidase activity using a guaiacol substrate was also measured at 470 nm as described in Buttery and Buzzell, Crop Science, 8:722–725 (1968). Measurement of known peroxidase solutions, shows this procedure does not give a linear response and is therefore not suitable for plant breeding (FIG. 3).

EXAMPLE 5

Method Comparison

In the ELISA procedure, we were unable to detect peroxidase with the 1:1000 and 1:5000 dilutions and the 1:100 dilution gave inconsistent results. Using the 1:10 dilution, we were able reproducibly to detect peroxidase. There was no increase in the optical density (OD) beyond 60 ng of peroxidase (FIG. 1).

In the PCA test, the 1:10000 dilution gave inconsistent results. Since the other dilutions gave similar results, the 1:5000 dilution was chosen because it uses the least amount of MAB (FIG. 2). Analysis of variance showed that a linear model explained the data ($R^2$=0.99).

Using a guaiacol substrate, peroxidase activity was measured at 470 nm (FIG. 3). Using analysis of variance, a linear model was inadequate to explain the data $R^2$=0.77).

ELISA and PCA Comparison

Boiled and nonboiled samples of purified peroxidase, were analyzed using both the ELISA and PCA assays. Presence or absence of peroxidase activities were checked using the guaiacol method (Buttery and Buzzell, 1968) (Table 1).

Analysis of Solutions With Known Peroxidase Activity

Figure 4:
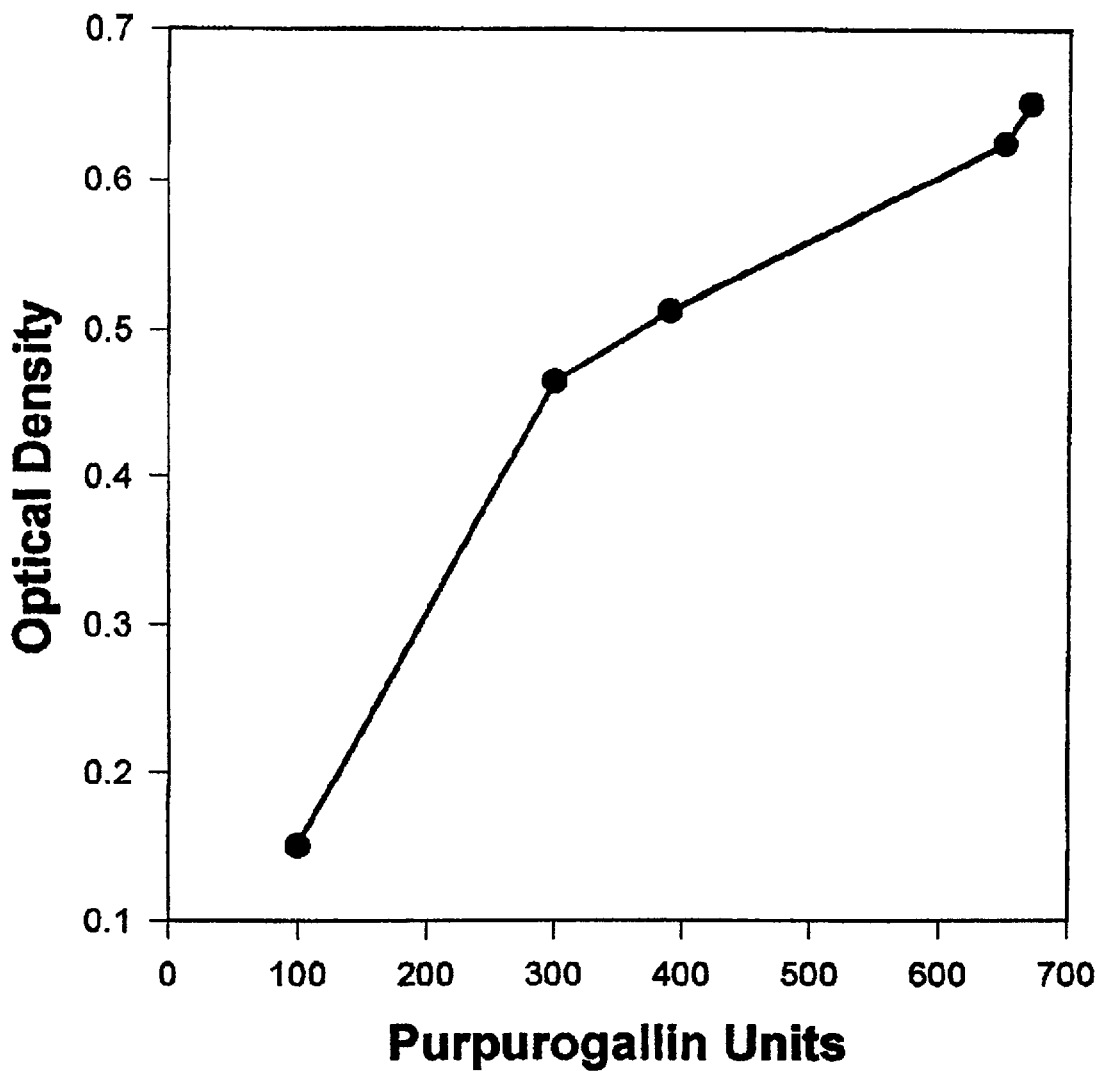
FIG. 4 Average PCA absorbance (450 nm) of peroxidase solutions of known activity against 1:5000 dilution of peroxidase MAB.

To determine if PCA could detect differences between samples with different peroxidase activities, samples with 100, 300, 390, 650, 670, 1500, and 2000 PPU/ml were analyzed using PCA (FIG. 4). There was no increase in the OD of the 1500 and 2000 PPU/ml samples over the 670 PPU/ml sample.

There was a major difference between what the PCA and ELISA techniques measured. The ELISA measures peroxidase concentration and not activity; the PCA measures activity not concentration. This was confirmed using the ELISA, PCA, and guaiacol procedures on boiled and nonboiled peroxidase samples. Comparison of the boiled and nonboiled OD of the guaiacol results obviously show the difference (Table 1). The guaiacol method showed high peroxidase activity in the nonboiled sample and no peroxidase activity in the boiled sample. The ELISA technique generated OD readings for both the boiled and nonboiled samples. There was a decrease in the ELISA OD between the boiled and nonboiled, which was probably attributable to destruction of the protein during the extended boiling of the sample. By comparison, the PCA OD was 0.0 in the boiled sample and 1.154 in the nonboiled sample. This is consistent with what one would expect looking at the differences between procedures. The ELISA technique used was a two-step indirect method. Conversely, in the PCA technique, peroxidase was captured by the peroxidase monoclonal antibody coating the sample well. There was no secondary enzyme-linked antibody in the reaction. The peroxidase chromogen was added directly to the bound peroxidase, which reacted with the chromogen. Therefore, the PCA technique measures activity and not peroxidase concentration. This is why the boiled sample, which had no activity, had no PCA OD reading. Since the antibody captured peroxidase maintains enzymatic activity, the antibody must bind to an epitope not involved with enzymatic activity.

Solutions with known differences in peroxidase activity were analyzed to confirm the result that PCA gives a quantitative measure of peroxidase activity. Results show that the PCA can detect differences in solutions containing various levels of known peroxidase activity (FIG. 4).

Peroxidase activity also may be measured using guaiacol as a substrate. Comparison of the peroxidase activity curves clearly showed a difference between this method and PCA. There was a linear relationship using PCA, but a linear model was not adequate to describe the relationship using the guaiacol method. A higher order model was needed to explain the guaiacol curve. We believe the PCA technique was superior since the relationship may be explained by a simpler model.

EXAMPLE 6 cDNA Library Construction

Total RNA was extracted from soybean (Glycine max cul. Resnik) seedbuds 21 days after flowering as previously described (20). Poly(A)-enriched RNA was prepared from total RNA using PolyATract and the cDNA library was constructed in the unidirectional vector Uni-ZAP XR.
Library Screening A plant peroxidase specific primer (PSP) was generated from a conserved amino acid region (distal heme ligand, HFHDCFV, SEQ ID NO 1) in all plant peroxidases (5'CA(C/T)TT(T/C)CA(C/T)GA(C/T)TG(C/T)TT(C/T)GT3') (SEQ ID NO 2). The probe was generated using the 3'RACE system with soybean seedbud total RNA and PSP as described by the manufacturer except that hot-start PCR was performed. The PCR-RACE products were cloned into pCR™II plasmid. DNA from twenty clones was purified and digested with EcoR I, fractionated by electrophoresis on a 1% agarose gel, and blotted on a nylon membrane that was probed with [γ-$^{32}$p]dATP-end-labeled PSP. A single positive clone was random prime labeled with [αx$^{32}$p]dCTP and used for primary screening of the cDNA library (2.5×10$^5$ PFU). Prehybridization was conducted in 6× SSPE, 5× Denhardt's, 0.5% (w/v) SDS, 100 µg/ml denatured salmon sperm DNA, and 50% formamide at 42° C. for two hours. Hybridizations were performed overnight and the conditions were the same as those in prehybridization except that 1× Denhardt's was used.

PCR using PSP and the T7 vector primer flanking the cloning site was used to purify single phage clones. Phage particles were eluted by incubating primary picks and/or single plagues in 500 µl of SM buffer (SM: 100 mM NaCl, 10 mM MgSO$_4$, 0.01% w/v gelatin in 50 mM Tris pH 7.5) at room temperature for 2 hours. The PCR cycling parameters were 94° C., 1 minute at 57° C., and 1 minute at 72° C., and followed by a final extension at 72° C. for 5 minutes. PCR reaction conditions were 1×reaction buffer (500 mM KCl, 100 mM Tris-HCl, pH 9.0, 1.0% Triton X-100), 1.5 mM MgCl$_2$, 200 µM each dNTPs, one unit of Taq DNA polymerase, 1 µM each primer and 2 µL of phage particle elution in 50 µL total.
DNA Sequencing and Sequence Analysis DNA sequencing of both strands was performed using Sequenase Kit 2.0 (USB) and SK and KS primers (Stratagene). Synthetic primers corresponding to internal sequences of cDNA were made to complete sequencing. Sequence data were analyzed using GCG software (Madison, Wis.).

EXAMPLE 7

Northern Blot Analysis and RT-PCR

Twenty-five µg of total RNA from various tissues were fractionated on 1% agarose gel containing formaldehyde, blotted onto nylon membrane, and probed with $^{32}$P labeled probe. Both prehybridization and hybridization conditions were the same as those described in library screening. Sample isolations and hybridizations were replicated twice.

cDNA specific primers designed from 3' untranslated regions of each cDNA and PSP were used in reverse transcript PCR (RT-PCR) to study expression patters. For SEPa1 (SEQ ID NO 10), SEPa2 (SEQ ID NO 12), SEPb1 (SEQ ID NO 14), and SEPb2 (SEQ ID NO 16) the primers were 5'AAATTAACTCAGCTGTGGG3' SEQ ID NO 3, 5'GGAACCCACTTATTCCATCG3' SEQ ID NO 4, 5'CCCAAGACATGCTTGAGAT3' SEQ ID NO 5, and 5'AAGTTCATACTTCTAAC3' SEQ ID NO 6, respectively.

Two µg of total RNA from different tissues of soybean were used for synthesizing the first strand of cDNA using SUPERSCRIPT™II Rnase H REVERSE TRANSCRIPTASE as suggested by the manufacture (BRL). RT-PCR conditions were the same as those in 3'RACE except that the annealing temperature for SEPb2 was 45° C.

EXAMPLE 8

Isolation of Soybean Peroxidase cDNAs

The conserved amino acid sequence of plant peroxidases enabled the generation of molecular probe for plant peroxidase genes using 3'RACE. The 3'RACE experiment with PSP and adaptor primer complimentary to the oligo-d(T) end of the cDNA resulted in amplification of a 900-bp DNA fragment (data not shown). Using the fragment as probe, 25 clones were obtained by primary hybridization screening. Eleven positive clones were recovered after two rounds of PCR using PSP and T7 vector primers, and four clones, designated SEPa1, SEPa2, SEPb1, and SEPb2, were further analyzed.
Sequence Analysis of the cDNAs The nucleotide sequences of the coding regions of SEPa1, SEPa2, SEPb1, and SEPb2, and their predicted amino acid sequences of their protein products, i.e., SEQ ID NOS 11, 13, 15, and 17, are shown in FIGS. 5A, 5B, 6A and 6B. The coding regions of SEPa1 and SEPa2 exhibit 97% amino acid identity, the coding regions of SEPb1 and SEPb2 have 95% amino acid identity, and the coding regions of SEPa1 and SEPb1 share 47% amino acid identity. Comparison of 168 bp, 3' untranslated regions of SEPa1 and SEPa2 revealed 83% homology. The homology between the 187 bp, 3' untranslated regions of SEPb1 and SEPb2 was 75%. There are 6 putative glycosylation sites specified by N-X-T/S at amino acid residues 56, 69, 128, 142, 183 and 214 in SEPa1 and SEPa2, and there are 4 putative glycosylation sites at residues 70, 142, 185 and 195 in SEPb1 and SEPb2, respectively; and SEPa1 and SEPa2 had the [Q L X X X F Y] SEQ ID NO 7 motif, where X is any amino acid, at the NH$_2$ terminus which is a feature found in most plant peroxidases. No [Q L X X X F Y] SEQ ID NO 7, motif exists in SEPb1 and SEPb2. Based on predicted amino acid sequences, all four proteins contain a predominantly hydrophobic amino acid signal sequences. Two copies of the putative polyadenylation signals AATAAG, SEQ ID NO 8 are present 39 and 106 bases upstream of the poly (A) signal in SEPa1 and 19 and 75 bases upstream in SEPa2. There is only one copy of the putative polyadenylation signal AATAAA 36 bases upstream of the poly (A) in SEPb 1 and 14 bases upstream in SEPb2.

EXAMPLE 9

Comparisons With Other Plant Peroxidase Sequences

Comparison between the predicted amino acid sequences of soybean peroxidases and some other plant peroxidase sequences. The levels of identity suggests that the clones encode peroxidases. There are three most highly conserved amino acid regions in almost all plant peroxidases. The first is from amino acid residues 33–55 with a predicted disulfide bridge in the middle and a potential heme binding site which belongs to a subdomain of 100% homology: HFHDCFV, SEQ ID NO 9. The second is from amino acid residues 89–105, again with two cysteines that may form disulfide bridges. The third is from amino acid residues 159–170 with a potential heme binding site in the middle. All of the peroxidases studied, except SEPb2, have eight cysteine residues that are located in similar positions in the primary sequences, and two invariable histidine residues (at positions 42 and 167 in soybean peroxidases, FIGS. 5A, 5B, 6A and 6B are inferred in the active-site structure. The number of glycosylation sites vary greatly according to the isozymes (from 1 in peanut PNC2, 3 and 6 in soybean, to 8 in horseradish).

Differential Expressions of Peroxidase mRNAs

Total RNA from leaf, stem, root, seedbud, and developing seed were probed with a 300bp Kpn-TifI fragment from the 3' untranslated region of SEPa1. Data reveals that transcripts of approximately 1400 nucleotides from SEPa1 are present in developing seed and root. Since both the coding regions and the noncoding regions of the four cDNAs are high homologous, RT-PCR experiments were conducted to study the differential expressions of peroxidase mRNA. Data shows the amplification of cDNA synthesized from total RNA of different tissues with PSP and SEPa1-specific primer. To confirm the identity of RT-PCR products, RT-PCR products were transferred to nylon membrane and hybridized with SEPa1 from which SEPa1-specific primer was designed. Based on the results of RT-PCR with cDNA-specific primers, transcripts from SEPa2 were also detected in root and developing seed, and transcripts from SEPb1 and SEPb2 were detected in root, stem, leaf, and seedpod.

EXAMPLE 10

Peroxidase Cloning

Our results demonstrate that PCR coupled with one round of conventional plaque lift hybridization was effective and rapid in both characterizing and screening of cDNA libraries provided that sequence information is available. This method would be especially useful when high density plating is used to obtain low abundance clones. Using PSP coupled with a vector primer, one can easily find the primary picks that are true positive clones. By replating the primary picks at low density, individual positive clones can be easily recovered by a second round of PCR with the same pair of primers. Directly using phage particle elution as template in PCR reactions without further precipitation was easily accomplished. The technique amplified a single, distinct product band from as few as $1\times10^6$ phage particles that corresponds to ~0.1 ng of DNA, or as many as $1\times10^8$ phage particles have been used under the same amplification conditions with no detectable loss of specificity. Another advantage of this method is the size of the insert of positive clones can be predicted. A gene-specific primer coupled with vector primer also can be used to reveal the presence of genes of interest in a library prior to screening due to the high sensitivity of PCR. Failure to amplify any product of interest from the library may indicate that full-length cDNA of interest is not likely to be present in the library. In such case, unproductive screening can be avoided.

The predicted amino acid sequences of the four cDNA exhibit homology to other plant peroxidases indicating that the clones encode peroxidase. Each enzyme, except SEPb2, has eight cysteines in nearly identical positions in the primary sequences. Similar cysteines in horseradish and turnip enzymes had been shown to be involved in intramolecular disulfide linkages. By analogy with horseradish and turnip sequences four intrachain disulfide linkages can be predicted in the soybean isoperoxidases SEPa1 and SEPa2 (cysteine pairs between residues 11/89, 44/49/, 95/298 and 174/207).

There are three highly conserved amino acid sequences in all plant peroxidases. The first and the third contain the distal and proximal histidine residues concerned with binding the heme group. The first critical histidine ligand in SEPa1, SEPa2, SEPb1, and SEPb2 occurs at amino acid 42 in the mature proteins, thought to act in acid/base catalysis, and the second at 167 thought to bind the 5th ligand of heme iron. His-42 and His-167 are almost at identical positions in all plant peroxidases.

Plant peroxidases differ greatly in the number and the position of putative glycosylation sites and the heterogeneity of glycosylation indicated that peroxidases exist in differently glycosylated forms or glycoforms. Variability in N-linked oligosaccharide chain location may be adaptively important for fine tuning catalytic properties of the functional enzyme molecule. However, a glycosylation site at residue 183 in SEPa1 and SEPa2 (185 in SEPb1 and SEPb2) is common to most plant peroxidases.

It is predicted from the cDNA sequences that all four proteins are initially synthesized as preproteins with predominantly hydrophobic amino acid signal sequences, suggesting that the mature proteins could be secreted through cell membranes. The hydrophobic residues in the signal peptides are of great importance and signal peptides are believed to function primarily by interacting favorably with the nonpolar interior of the membrane, entering and spanning it. All cloned plant peroxidases so far have a signal peptide and are therefor targeted to the secondary pathway. This was confirmed by biochemical studies of tobacco peroxidases localizing the peroxidases with pI 7.2–7.5 to the vacuoles and acidic peroxidases to the cell walls. It was reported that a C-terminal propeptide of 15 residues was necessary for proper sorting of barley lectin to vacuoles and that the vacuolar protein had this signal removed. Comparison of horseradish C protein and the cDNA derived sequences showed that 15 residues were removed at the C-terminus. The deduced amino acid sequences of soybean peroxidases showed no C-terminal extension present in peroxidases targeted to the vacuole.

Soybean peroxidases SEPb1 and SEPb2 may represent a new family of plant peroxidases and, perhaps, a new, unique biological function, as it is less than 50% amino acid identical to other known peroxidases. Cluster analysis of 2 plant peroxidases showed that SEPb1 and SEPb2 form a distinct group. SEPa1 and SEPa2 show about 67% amino acid identity to tomato anionic peroxidases tap1 and tap2. Using tap1 or tap2 promoter/GUS fusions, the indution of the peroxidase genes by wounding and pathogen attack has been reported, (Mohan, et al., Plant Molecular Biology 21:341–354, 1993). This suggests a role of these peroxidase genes in wound healing process and in the plant defense response. A root-specific peroxidase gene has been described in Nicotiana sylvestris and its expression was initially linked to the initiation of the cell cycle of in vitro cultured protoplasts. Acidic tobacco peroxidase TOP A is a constitutive, cell wall bound peroxidase most abundant in root and stem and thought to participate in secondary cell wall thickening. Over-expression of TOP A in transgenic tobacco gave rise to light-dependent wilting. A powdery mildew induced peroxidase pPOX381 of wheat leaves is about 90% identical to a constitutive wheat root peroxidase. The pPOX381 is 57% identical to TP 7, a highly basic peroxidase of the evolutionarily remote turnip, suggesting that these peroxidases might share common functional roles. These very different characteristics of plant peroxidase families may indicate that peroxidases have evolved to participate in very different biological functions.

Our results showed that RT-PCR with gene-specific primers is an effective and sensitive way to study expression of highly homologous genes. The result of RT-PCR was the same as that of Northern blotting, but RT-PCR in which 2 μg of total RNA was used is more sensitive than Northern blot in which 25 μg of total RNA was used in detection of gene expression. The expression patterns of the genes obtained from both northern analysis and RT-PCR indicates differential expressions of various genes. In studies of other plants, there was evidence of differential expression of peroxidase genes. It is not apparent why some organisms have a relatively large number of expressed peroxidase genes. One possibility is that the different encoded proteins have different functions. However, different isoforms can be produced by post-translational modification, suggesting that different genes might not be necessary to provide different functions. A second possibility is that multiple genes could allow for greater regulatory flexibility. Some genes may be expressed in specific organs or at specific stages, and the expression of the genes may be determined by different signals. Regulations studies of the different peroxidase genes and the specific functions of their products are under way.

EXAMPLE 11

Detection of Soybean Cyst Nematode Feeding

Soybean cyst nematode (SCN) is a major pest of soybean, which decreases yield by feeding on roots. Seedlings from 4 SCN resistant and 2 susceptible cultivars were challenged with 3000 SCN juveniles. Control seedlings were not challenged with SCN. Samples were collected at 0, 1, 2, 3 and 4 weeks and peroxidase activity assayed according to example 3. There was no increase in peroxidase activity at weeks 1 and 2. There was increased peroxidase activity in all cultivars at week 3 (range 3 to 89%). At week 4 the increase in activity ranged from 4 to 41%. By week 5 there was no increased peroxidase activity in the SCN challenged samples. Samples were taken from root tissue.

EXAMPLE 12

Quantitation of Peroxidase Activity in Stored Seeds

Seeds from high peroxidase soybean cultivars were stored under various conditions to determine factors that affect peroxidase activity. Two replicates of seed lots were stored at 10° C., 20° C., 30° C., 40° C. and warehouse conditions. Seed were equilibrated to moistures of 9 and 13%. Samples were drawn monthly except for 40° C., which was drawn weekly. Peroxidase activity was determined according to Example 3. Results show that the greater the temperature, the greater the decrease in peroxidase activity.

EXAMPLE 13

Immunopurification of Peroxidase

Peroxidase was purified from plant fluid and solutions by immunoprecipitation. Solutions containing peroxidase were mixed with said antibody. Protein A-Sepharose was added to the peroxidase/antibody mixture and incubated for one hour at 4° C. The tertiary protein A—peroxidase antibody complex was collected by centrifugation and washed three times. The resuspended sepharose beads were incubated at 4° C. for 20 minutes. After the last wash, 30 μl of gel-loading buffer was added to the beads. Samples were heated to 100° C. for 3 minutes and the protein A-sepharose was removed by centrifugation. Purified proteins were separated on a nondenaturing acrylamide gel and visualized by histochemical staining using tetramethylbenzadine as a chromogen. Results shaved a single peroxidase band on the gel.

EXAMPLE 14

Crop and Cultivar Screening

Figure 7:
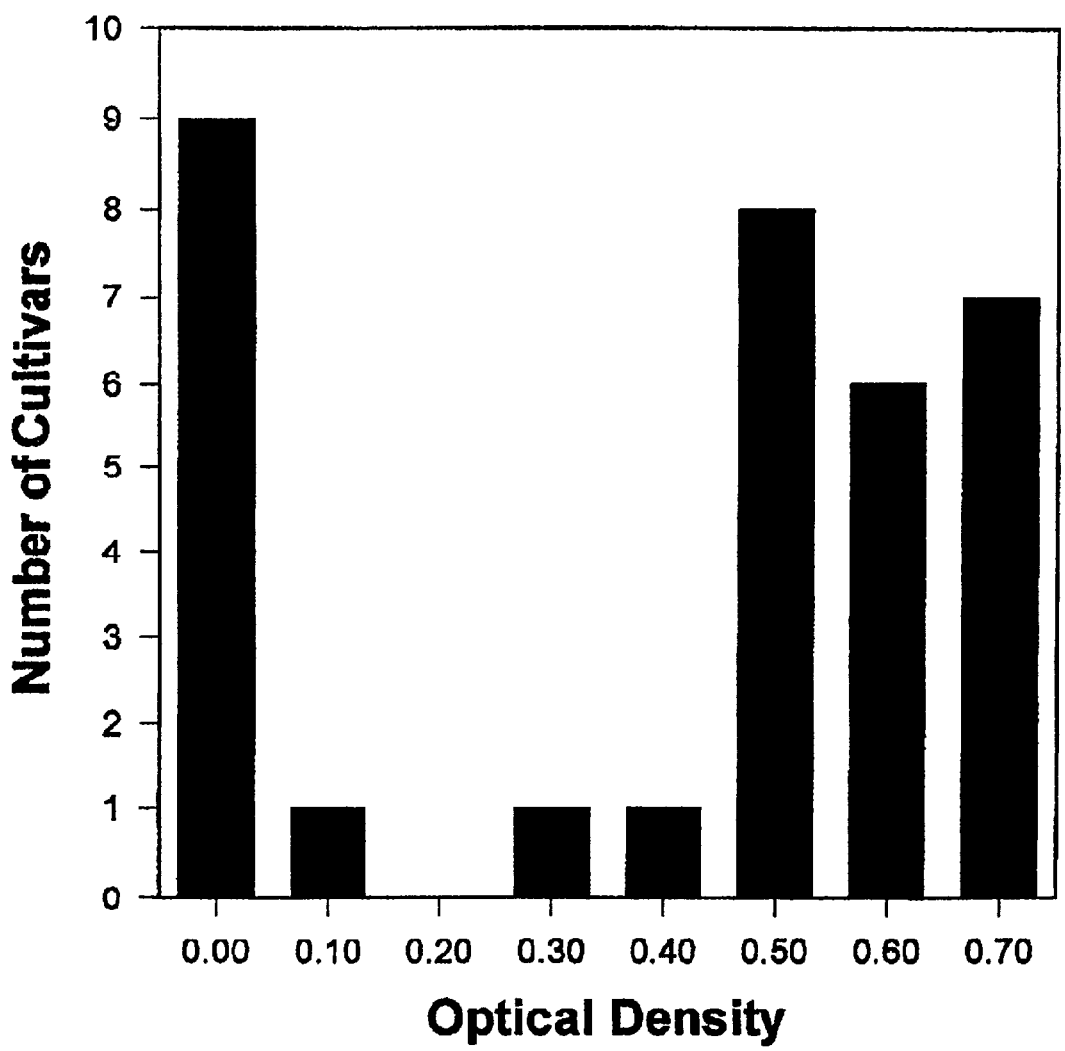
FIG. 7 Histogram of average SPCA absorbance of cultivars.
Figure 8:
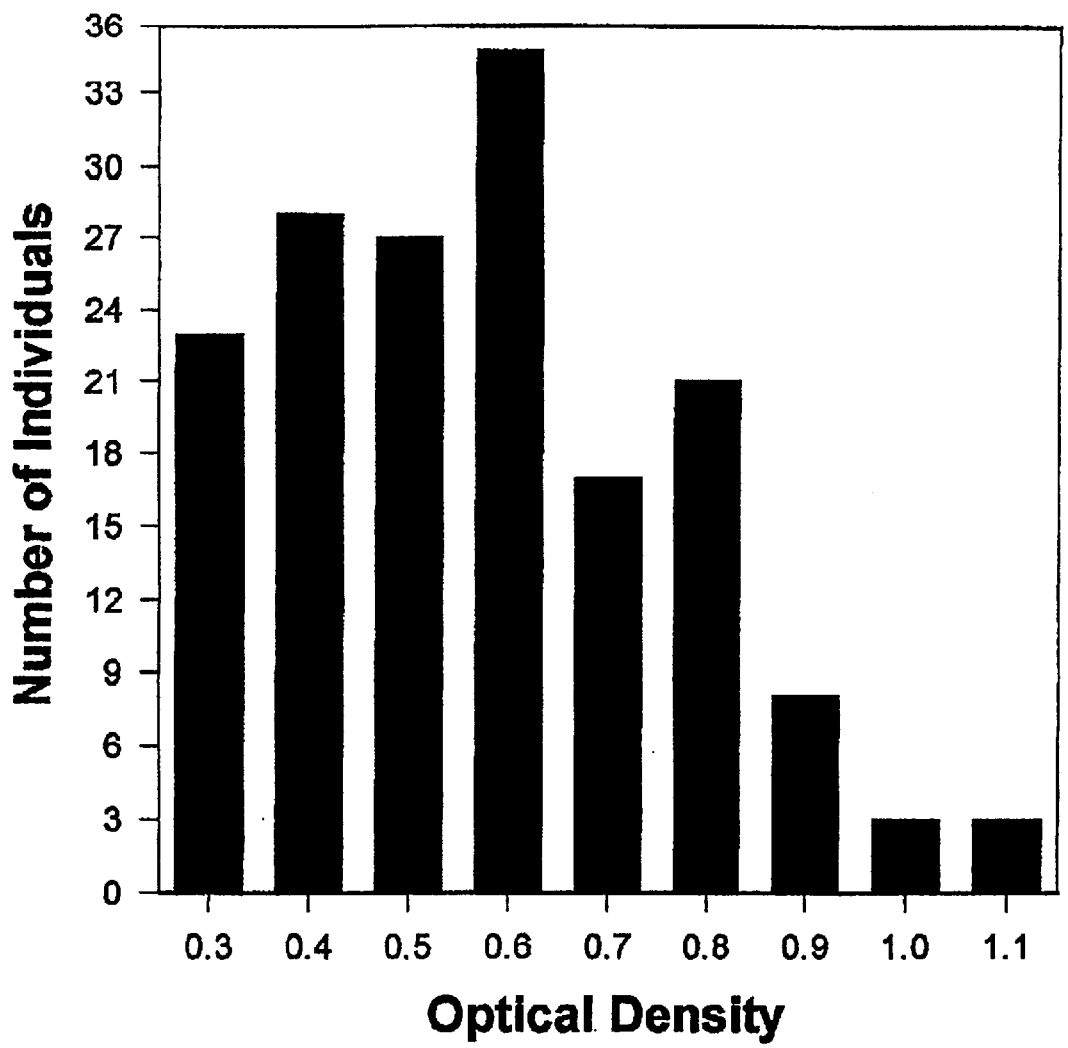
FIG. 8 Histogram of average absorbance of genotypes within an $F_3$ segregating population. Optical density values were 0.777 for Resnik and 0.502 for Winchester.

The use of said antibody is not limited to soybean. In soybeans though, 306 plant introductions from USDA and 33 cultivars were screened for peroxidase activity (FIG. 7). The invention is also useful for screening segregating populations as in a plant breeding program. The means from three replications of the high-peroxidase cultivars used as parents in the cross, Winchester and Resnik, were 0.502±0.038 and 0.777±0.082 respectively. PCA detected differences in a segregating population (FIG. 8). One hundred fifteen progeny from a cross of two high peroxidase cultivars were screened for peroxidase activity. Genotypes with peroxidase activity higher than both parents were identified. The said invention also detected differences in peroxidase activity between 9 sorghum, 5 wheat, 5 corn and 2 oat cultivars.

Analysis of the segregating population showed that PCA can detect differences in peroxidase activity and genotypes with activity greater than the highest parent were identified. PCA will therefore be useful in the introgression of high peroxidase activity into breeding lines. The PCA technique uses the same equipment as the ELISA technique and large scale screening will therefore be routinely available. Results show that peroxidase can be easily extracted from seed coats without destroying the seed. Besides being a valuable procedure for screening cultivars for high peroxidase activity, this technique also will permit investigations of the effect environment and seed storage have on peroxidase activity.

EXAMPLE 15

Increased Peroxidase Activity in Plants

Peroxidase activity can be increased through plant breeding as described in Example 14. Another method is through plant transformation. Duplicate copies of the gene may be incorporated into plants. Another manifestation is the transformation of altered or mutant copies of the gene. DNA sequences may be altered by means of in vitro mutagenesis and alteration of the regulatory regions, promoter, 5'- and 3' untranslated regions, coding regions or termination sequences may increase expression of the peroxidase gene. Transformation and production of peroxidase is not limited to soybeans and may be accomplished in plants that are transformable.

EXAMPLE 16

Production of Peroxidase in Bacteria

A single recombinant colony was incubated overnight at 37° C. in 3 ml of LB medium containing 100 μg/ml ampicillin. One ml of culture was used to inoculate 50 ml of fresh LB containing ampicillin and allowed to grow to an $OD_{600}$=0.5. IPTG was added to a final concentration of 0.5 mM and incubated for an additional 4 hours. Two hundred μl of the culture was pelleted by centrifugation and resuspended in 100 μl of TE. Bacteria was homogenized for 45 seconds with an acetal pestle. The homogenate was centrifuged and 50 μl of the supernatant was analyzed on both an acrylamide gel and the invention as stated in example 3. Functional peroxidase was isolated from bacterial cultures.

EXAMPLE 17

Genomic Library Construction and Screening

Soybean nuclear DNA was restriction digested with Xho I and ligated into Xho I digested EMBL3 SP6/T7 lambda arms (Stratagene). The genomic library was screened by one round of lift hybridization and positive clones were purified by two rounds of PCR screening. For lift hybridizations, $5\times10^5$ plaques were plated and hybridized with a mixture of $^{32}$P-dCTP randomly labeled cDNAs from example 6. Two rounds of PCR screening were performed on 14 clones to purify positive clones. PCR primers designed from 5' and 3' ultratranslated regions of the 4 cDNAs (examples 6 and 8) were used in PCR screening. Four genomic clones were recovered.

EXAMPLE 18

Production of Transgenes in Soybean

Transformed plants comprising a recombinant DNA sequence under modified or unmodified transcriptional and translational control of the peroxidase promoter and containing the hydrophobic leader sequence and a sequence encoding a protein or polypeptide will be expressed in the seed coat. Expressed transgenes may be antigenic and act as an animal or human vaccine. Transgenes also may be enzymes or nonenzymatic proteins.

EXAMPLE 19

Solid-Phase Peroxidase

Peroxidase captured by the said antibody still maintains oxidative activity, therefore antibody bound peroxidase can be immobilized on a solid state matrix (e.g. polystyrene, sepharose column). In oxidative reactions where peroxidase is being used, reagents may be passed through or over immobilized peroxidase and product or modified reagents collected.

EXAMPLE 20

Non-radioactive Detection of Nucleic Acids

Peroxidase can be covalently conjugated to oligonucleotides. This conjugate can be used as a probe in hybridization assays and in polymerase chain reaction procedures as described in Pat. Nos. 5,254,469 and 5,272,077. The said antibody can be used to purify the oligonucleotide peroxidase conjugate (Example 13). Said antibody may be conjugated with enzyme, such as peroxidase, glucose oxidase, alkaline phosphatase and beta-galactosidase and used in the detection of nucleic acid providing an appropriate chromogen, fluorogen, chemiluminescent or substrate is provided.

While the invention has been disclosed in this patent application by reference to the details of the preferred embodiments of the invention, it is to be understood that this disclosure is intended in an illustrative rather than a limiting sense, as it is contemplated that modifications will readily occur to those skilled in the art, within the spirit of the invention and the scope of the appended claims.

What is claimed is:

1. An isolated soybean DNA comprising cDNA coding for an SEPa1 polypeptide wherein said SEPa1 polypeptide comprises the amino acid sequence set forth in Seq ID NO:11.

2. A pair of single-stranded DNA primers, wherein the sequence of said primers is derived from the sequence set forth in SEQ ID NO: 10, wherein the use of said primers in a polymerase chain reaction results in the synthesis of DNA having all or part of the sequence of the SEPa1 gene.

3. A soybean nucleic acid probe complementary to SEPa1 gene sequence, wherein said SEPa1 gene sequence comprises the nucleic acid sequence set forthe in Seq ID NO:10.

4. A replicative cloning vector which comprises the isolated DNA of claim 1 and a replicon operative in a host cell.

5. A replicative cloning vector which comprises the isolated DNA of claim 2 and a replicon operative in a host cell.

6. An expression system which comprises the isolated DNA of claim 1 operably linked to suitable control sequences.

7. An expression system which comprises the isolated DNA of claim 2 operably linked to suitable control sequences.

8. Recombinant host cells transformed with the expression system of claim 6.

9. Recombinant host cells transformed with the expression system of claim 7.

10. A method of producing recombinant SEPa1 polypeptide which comprises culturing the cells of claim 8 under conditions effective for the production of said SEPa1 polypeptide.

* * * * *